(12) United States Patent
Harada

(10) Patent No.: US 9,187,632 B2
(45) Date of Patent: *Nov. 17, 2015

(54) NON-SPHERICAL RESIN PARTICLES, MANUFACTURING METHOD THEREOF, AND USE THEREOF

(75) Inventor: Ryosuke Harada, Koka (JP)

(73) Assignee: Sekisui Plastics Co., Ltd., Osaka-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/240,410

(22) PCT Filed: Aug. 27, 2012

(86) PCT No.: PCT/JP2012/071558
§ 371 (c)(1),
(2), (4) Date: Feb. 24, 2014

(87) PCT Pub. No.: WO2013/027849
PCT Pub. Date: Feb. 28, 2013

(65) Prior Publication Data
US 2014/0194565 A1    Jul. 10, 2014

(30) Foreign Application Priority Data
Aug. 25, 2011 (JP) .................. 2011-184018

(51) Int. Cl.
*C08L 33/14* (2006.01)
*C08F 2/22* (2006.01)
(Continued)

(52) U.S. Cl.
CPC .............. *C08L 33/14* (2013.01); *A61K 8/0245* (2013.01); *A61K 8/8152* (2013.01); *A61Q 1/02* (2013.01);
(Continued)

(58) Field of Classification Search
CPC .............. C08L 33/14; C08F 2/22; C08J 3/12; A61K 8/02; A61K 8/81; A61K 28/14; A61Q 1/02
USPC .................... 524/556, 520; 525/200
See application file for complete search history.

(56) References Cited

U.S. PATENT DOCUMENTS

2009/0035578 A1    2/2009   Watanabe et al.

FOREIGN PATENT DOCUMENTS

| EP | 2415786 A1 | 2/2012 |
|---|---|---|
| JP | 10-060011 A | 3/1998 |

(Continued)

OTHER PUBLICATIONS

International Search Report dated Nov. 27, 2012, issued for PCT/JP2012/071558.
(Continued)

*Primary Examiner* — Michael M Bernshteyn
(74) *Attorney, Agent, or Firm* — Locke Lord LLP; James E. Armstrong, IV; Nicholas J. DiCeglie, Jr.

(57) ABSTRACT

Disclosed are non-spherical resin particles that allow for improvement of light diffusion, light reflection, and other related properties, and a manufacturing method thereof. The particles have a circular outline when viewed from a direction in which a maximum projected area is produced and a non-circular outline when viewed from a direction in which a minimum projected area is produced, The particles comprise first and second, different resin components (1) and (2), with the second resin component (2) residing locally near the surface of the non-spherical resin particles. The method of manufacturing non-spherical resin particles involves either allowing particles of a resin to absorb a vinyl-based polymerizable monomer contained in an aqueous emulsion followed by polymerization of the absorbed monomer or dissolving a resin in a vinyl-based polymerizable monomer followed by polymerization of the obtained solution in an aqueous medium.

15 Claims, 20 Drawing Sheets

(51) Int. Cl.
*C08J 3/12* (2006.01)
*A61K 8/02* (2006.01)
*A61Q 1/02* (2006.01)
*A61K 8/81* (2006.01)
*G02B 5/02* (2006.01)

(52) U.S. Cl.
CPC . *C08F 2/22* (2013.01); *C08J 3/126* (2013.01); *A61K 2800/412* (2013.01); *G02B 5/0242* (2013.01)

(56) References Cited

FOREIGN PATENT DOCUMENTS

| JP | 11-140139 | A | | 5/1999 |
|----|-----------|---|---|--------|
| JP | 2004-027008 | A | | 1/2004 |
| JP | 2007-197588 | A | | 8/2007 |
| JP | 2010-001331 | A | | 1/2010 |
| JP | 2011-006664 | A | | 1/2011 |
| JP | 2011006664 | A | * | 1/2011 |
| JP | 2011-105909 | A | | 6/2011 |
| JP | 2011105909 | A | * | 6/2011 |
| JP | 2011-219744 | A | | 11/2011 |
| WO | WO-2009/051256 | A1 | | 4/2009 |
| WO | WO-2010/113812 | A1 | | 10/2010 |
| WO | WO 2010113812 | A1 | * | 10/2010 |

OTHER PUBLICATIONS

Extended European Search Report issued in European Patent Application No. EP 12825843.0, dated Mar. 12, 2015.

T. Tanaka et al. "Preparation of "Mushroom-like" Janus Particles by Site-Selective Surface-Initiated Atom Transfer Radical Polymerization in Aqueous Dispersed Systems." Langmuir 2010, 26(11), 7843-7847.

* cited by examiner (a)

(b)

(c)

(a)

(b)

(c)

(a)

(b)

(c)

(a)

(b)

(c)

NON-SPHERICAL RESIN PARTICLES, MANUFACTURING METHOD THEREOF, AND USE THEREOF

TECHNICAL FIELD

The present invention relates in general to non-spherical resin particles, manufacturing methods thereof, and uses thereof (emulsifiers, external preparations, emulsions, coating agents, light diffusers, and optical members) and in particular to non-spherical resin particles containing two distinct resin components with one of the resin components residing locally near the surface of the non-spherical resin particles, as well as to manufacturing methods and uses thereof.

BACKGROUND ART

Conventional non-spherical resin particles are known that are composed of two or more different resin components.

Patent Document 1, as an example, describes use of a phase separation mechanism in a method in which a mixture is prepared by mixing: a polymer compound obtained by polymerization of a methacrylic acid ester; a methacrylic acid ester; and a radical polymerization initiator, and the mixture is subjected to suspension polymerization in an aqueous solution containing a dissolved dispersion stabilizer. Examples 8 and 9 given in the document produce acrylic resin particles with dimples, shaped overall like golf balls. Example 10 produces partially porous acrylic resin particles with numerous less-than-1-micrometer dents.

Another example, Patent Document 2, describes fine spherical polymer particles with a regularly creased surface being produced by dissolving a styrene-based elastomer in a mixture of a hydrophobic polymerizable vinyl monomer and a crosslinking monomer and subjecting the dissolved elastomer to suspension polymerization in an aqueous medium.

CITATION LIST

Patent Literature

Patent Document 1: Japanese Patent Application Publication, Tokukaihei, No. 10-60011
Patent Document 2: Japanese Patent Application Publication, Tokukaihei, No. 11-140139

SUMMARY OF THE INVENTION

Problems to be Solved by the Invention

The shapes of the non-spherical resin particles described in Patent Documents 1 and 2 are, however, limited to golf ball-like dimpled spheres, spheres with a porous surface area, and spheres with a regularly creased surface. All of these particles are practically spherical, giving the same outline from whichever direction they are viewed. None of the particles are shape-anisotropic or non-spherical. In addition, although Patent Documents 1 and 2 do not disclose in which part of the non-spherical resin particle each resin component of the non-spherical resin particle is present or absent, it is inferred from the isotropic shape of the non-spherical resin particle that the resin components of the non-spherical resin particle are isotropically present. From these facts and inferences, the non-spherical resin particles of Patent Documents 1 and 2 are not expected to anisotropically diffuse or reflect light at their surfaces or resin/component interfaces. It is therefore unlikely that light diffusion and other related properties could be improved by the anisotropy of the surfaces or resin/component interfaces of the non-spherical resin particles.

In view of these challenges, it is an object of the present invention to provide non-spherical resin particles that allow for improvement of light diffusion, light reflection, and other related properties, and also to provide a manufacturing method thereof and a use thereof (emulsifiers, external preparations, emulsions, coating agents, light diffusers, and optical members).

Solution to Problem

Non-spherical resin particles in accordance with the present invention, to address the problems, are non-spherical resin particles, each having a circular outline when viewed from a direction in which a maximum projected area is produced and a non-circular outline when viewed from a direction in which a minimum projected area is produced, each of the non-spherical resin particles including a first resin component and a second resin component which is different from the first resin component, the second resin component residing locally near a surface of that particle.

The non-spherical resin particles thus structured are shape-anisotropic because they have a circular outline when viewed from a direction in which a maximum projected area is produced and a non-circular outline when viewed from a direction in which a minimum projected area is produced. Therefore, the light diffusion, light reflection, and other related effects of the surface of the non-spherical resin particles are anisotropic. As a result, the non-spherical resin particles thus structured exhibit improved light diffusion, light reflection, and other related properties.

Furthermore, according to the structure, the second resin component, which is different from the first resin component, resides locally near the surface of the non-spherical resin particles. Therefore, the portions made of the two distinct resin components (first and second resin components) are present locally in a single non-spherical resin particle. The interface of these portions, which are present locally in a single non-spherical resin particle, for example, diffuses (scatters) and reflects light. As a result, the non-spherical resin particles thus structured exhibit improved light diffusion, light reflection, and other related properties, when compared with resin particles composed of conventional single resin components.

Besides, in the non-spherical resin particles thus structured, the second resin component resides locally near the surface of the non-spherical resin particles, and the second resin component is present anisotropically. Therefore, the light diffusion, light reflection, and other related effects of the interface are anisotropic. As a result, the non-spherical resin particles thus structured exhibit further improved light diffusion, light reflection, and other related properties.

Throughout the present specification, "the second resin component residing locally near the surface of a non-spherical resin particle" means that if the non-spherical resin particle is divided into two fragments by a cross-section including the center of mass of the non-spherical resin particle (e.g., a cross-section normal to a direction in which a maximum projected area is produced), the second resin component is present in a greater amount in one of the fragments than in the other fragment.

Preferably, in the non-spherical resin particles in accordance with the present invention, each of the non-spherical resin particles has a partly missing sphere shape, the missing part has a surface at least a portion of which is formed of the second resin component, and the rest of the surface of the particle is formed of the first resin component.

According to the structure, a portion of the surface of the particle is formed of the first resin component, and the rest of the surface is formed of the second resin component. Therefore, the surface of the particle has different portions having different properties: for example, a hydrophilic portion of the surface and a hydrophobic portion of the surface. The resin particles with a surface exhibiting different properties in different portions thereof may, by exploiting these surface properties, be applicable to diagnostic medicinal particles, medical base material, biocompatible material, dental material, cosmetic base material, anti-pollution paint, antifog material, charge inhibitor, electrically conductive adhesive, electrically conductive sealing material, magnetic particles, storage media, and chromatographic filling material, to name a few examples.

In addition, according to the structure, the second resin component forms at least a portion of the surface of the missing part of the non-spherical resin particle. If the missing part of the non-spherical resin particle forms a notch section (concave section), the particle can selectively adsorb and hold specific components that have high affinity with the second resin component in the notch section.

Preferably, the non-spherical resin particles in accordance with the present invention are semi-spherical, shaped like a biconvex lens, shaped like a mushroom, or have a horseshoe-like cross-section.

According to the structure, the particles have highly non-spherical shapes. Therefore, the particles exhibit further improved light diffusion, light reflection, and other related properties.

Furthermore, in the non-spherical resin particles with a horseshoe-like cross-section, the portion made of the second resin component may be localized to the notch section. The structure enables the particles to selectively adsorb and hold specific components that have high affinity with the second resin component in the notch section.

Preferably, in the non-spherical resin particles in accordance with the present invention, the first resin component is a hydrophilic resin, and the second resin component is a hydrophobic resin.

In the non-spherical resin particles thus structured, a portion made of a hydrophilic resin and a portion made of a hydrophobic resin are present locally in a single non-spherical resin particle. Therefore, a portion of the surface is formed of a hydrophilic resin component, and the rest of the surface is formed of a hydrophobic resin component. As a result, the non-spherical resin particles thus structured have a surface that is partly hydrophilic and partly hydrophobic. The particles are thus suited for the variety of applications listed above.

According to the structure, in the case of non-spherical resin particles whose surface has two externally facing portions, such as semi-spherical, biconvex lens-shaped, or mushroom-shaped particles, a portion of the surface is either entirely or primarily formed of a hydrophobic resin, and the other portion of the surface is either entirely or primarily formed of a hydrophilic resin. In this structure, one of the portions may be hydrophobic, and the other portion may be hydrophilic. When this is actually the case, the non-spherical resin particles can be readily arranged on a base material by exploiting the different properties of the two portions.

In addition, according to the structure, a portion of the surface is formed of a hydrophobic resin, and the rest of the surface is formed of a hydrophilic resin. Therefore, a portion of the surface is hydrophobic, and the rest of the surface is hydrophilic. As a result, if the non-spherical resin particles thus structured are disposed at the interface of liquids with different hydrophilicity (different hydrophobicity), such as a water/oil interface, an end of each particle is oriented toward the relatively hydrophilic liquid, and the other end of the particle is oriented toward the relatively hydrophobic liquid, forming an oriented film. Since the oriented film reduces interfacial tension, the non-spherical resin particles thus structured also act as a surfactant.

A method of manufacturing non-spherical resin particles in accordance with in accordance with the present invention, to address the problems, includes either the set of steps of allowing particles of a resin to absorb a vinyl-based polymerizable monomer contained in an aqueous emulsion; and polymerizing the absorbed vinyl-based polymerizable monomer or the set of steps of: dissolving a resin in a vinyl-based polymerizable monomer to prepare a solution; and polymerizing the solution in an aqueous medium, wherein: the resin has a moiety derived from a (meth)acrylic acid ester having in an ester moiety thereof a $C_2$-$C_{10}$ halogenated alkyl group or alicyclic hydrocarbon group and has a weight-average molecular weight of from 150,000 to 1,000,000 as measured by gel permeation chromatography; and the vinyl-based polymerizable monomer contains a crosslinking monomer in an amount of 5 to 50 wt % as based on a total amount of the vinyl-based polymerizable monomer.

According to the method, the resin has a moiety derived from a (meth)acrylic acid ester having in an ester moiety thereof a $C_2$-$C_{10}$ halogenated alkyl group or alicyclic hydrocarbon group. Therefore, the resin is highly hydrophobic and likely to phase-separate from the polymer of the vinyl-based polymerizable monomer during the polymerization of the vinyl-based polymerizable monomer. The resin is hence likely to reside locally near the surface of the non-spherical resin particles.

In addition, according to the method, the resin has a weight-average molecular weight of 150,000 or greater. Therefore, the resin is likely to phase-separate from the polymer of the vinyl-based polymerizable monomer during the polymerization of the vinyl-based polymerizable monomer. The resin is hence likely to reside locally near the surface of the non-spherical resin particles. In addition, according to the method, the resin has a weight-average molecular weight of 1,000,000 or less. Therefore, the resin either sufficiently absorbs the vinyl-based polymerizable monomer or sufficiently dissolves in the vinyl-based polymerizable monomer.

In addition, according to the method, the vinyl-based polymerizable monomer contains a crosslinking monomer in an amount of 5 to 50 wt % as based on the total amount of the vinyl-based polymerizable monomer. Therefore, the resin is likely to phase-separate from the polymer of the vinyl-based polymerizable monomer during the polymerization of the vinyl-based polymerizable monomer. The resin is hence likely to reside locally near the surface of the non-spherical resin particles.

As described in the foregoing, according to the method, the vinyl-based polymerizable monomer is likely to phase-separate from the resin during the polymerization of the vinyl-based polymerizable monomer. Therefore, the vinyl-based polymerizable monomer is likely to reside locally near the surface of the non-spherical resin particles and either is sufficiently absorbed by particles of the resin or sufficiently dissolves the resin. The synergistic effect of these features enables the manufacture of non-spherical resin particles in accordance with the present invention, each having a circular outline when viewed from a direction in which a maximum projected area is produced and a non-circular outline when viewed from a direction in which a minimum projected area is produced, each of the non-spherical resin particles including a first resin component and a second resin component which is different from the first resin component, the second resin component residing locally near a surface of that particle.

Throughout the present specification, "(meth)acrylic" encompasses both "acrylic" and "methacrylic," and "(meth) acrylate" encompasses both "acrylate" and "methacrylate." In addition, throughout the present specification, "a moiety derived from a (meth)acrylic acid ester having in an ester moiety thereof a $C_2$-$C_{10}$ halogenated alkyl group or alicyclic hydrocarbon group" refers to one or more repeat units obtained by polymerizing a (meth)acrylic acid ester having in an ester moiety thereof a $C_2$-$C_{10}$ halogenated alkyl group or alicyclic hydrocarbon group.

An emulsifier in accordance with the present invention includes the non-spherical resin particles in accordance with the present invention. If either one of the first and second resin components of the non-spherical resin particles is a hydrophobic resin, and the other is a hydrophilic resin, the non-spherical resin particles can function as an emulsifier.

An external preparation in accordance with the present invention includes the non-spherical resin particles in accordance with the present invention.

If one of the first and second resin components of the non-spherical resin particles is a hydrophobic resin, and the other is a hydrophilic resin, the non-spherical resin particles can function as an emulsifier. Therefore, if the external preparation in accordance with the present invention is an emulsion containing an aqueous phase component and an oil phase component, the external preparation in emulsion form exhibits excellent emulsification stability and requires no use of surfactant.

An emulsion in accordance with the present invention includes the non-spherical resin particles in accordance with the present invention.

If either one of the first and second resin components of the non-spherical resin particles is a hydrophobic resin, and the other is a hydrophilic resin, the emulsion in accordance with the present invention exhibits excellent emulsification stability and requires no use of surfactant because the non-spherical resin particles function as an emulsifier.

A coating material in accordance with the present invention includes the non-spherical resin particles in accordance with the present invention.

The coating material in accordance with the present invention exhibits excellent light diffusion properties and imparts excellent flatting properties to coatings when used as a top coating paint, because the coating material includes the non-spherical resin particles in accordance with the present invention which exhibit excellent light diffusion properties.

A light diffuser in accordance with the present invention includes the non-spherical resin particles in accordance with the present invention.

The light diffuser exhibits excellent light diffusion properties because the light diffuser includes the non-spherical resin particles in accordance with the present invention which exhibit excellent light diffusion properties.

An optical member in accordance with the present invention includes a base material and the non-spherical resin particles in accordance with in accordance with the present invention, wherein the non-spherical resin particles are semi-spherical and arranged on the base material so that plane portions thereof face the base material.

According to the structure, the non-spherical resin particles are arranged on the base material so that their plane portions face the base material. Hence, the optical member controls the direction of the light diffused at the surface of the non-spherical resin particles so that the diffused rays travel in directions closer to the normal to the base material surface (front direction), or in other words, converges the diffused rays so that they travel in directions closer to the front direction. Therefore, when the optical member thus structured is incorporated into optical apparatus (e.g., a liquid crystal display device), the optical member will improve the luminance of the optical apparatus in the front direction (luminance observed when viewed normal to the front face of the optical apparatus). In addition, the optical member thus structured exhibits excellent light diffusion properties because the optical member includes the non-spherical resin particles in accordance with the present invention which exhibit excellent light diffusion properties.

Advantageous Effects of the Invention

As described in the foregoing, the present invention provides non-spherical resin particles that allow for improvement of light diffusion, light reflection, and other related properties, and also provides a manufacturing method thereof and a use thereof (emulsifiers, external preparations, emulsions, coating agents, light diffusers, and optical members).

BRIEF DESCRIPTION OF DRAWINGS

FIG. 1(a) shows a projection of the non-spherical resin particle as viewed from a direction in which a maximum projected area is produced. FIG. 1(b) shows a projection of the non-spherical resin particle as viewed from a direction in which a minimum projected area is produced. FIG. 1(c) is a cross-sectional view of the non-spherical resin particle taken normal to the direction in which a minimum projected area is produced.

FIG. 2(a) shows a projection of the non-spherical resin particle as viewed from a direction in which a maximum projected area is produced. FIG. 2(b) shows a projection of the non-spherical resin particle as viewed from a direction in which a minimum projected area is produced. FIG. 2(c) is a cross-sectional view of the non-spherical resin particle taken normal to the direction in which a minimum projected area is produced.

FIG. 3(a) shows a projection of the non-spherical resin particle as viewed from a direction in which a maximum projected area is produced. FIG. 3(b) shows a projection of the non-spherical resin particle as viewed from a direction in which a minimum projected area is produced. FIG. 3(c) is a cross-sectional view of the non-spherical resin particle taken normal to the direction in which a minimum projected area is produced.

FIG. 4(a) shows a projection of the non-spherical resin particle as viewed from a direction in which a maximum projected area is produced. FIG. 4(b) shows a projection of the non-spherical resin particle as viewed from a direction in which a minimum projected area is produced. FIG. 4(c) is a cross-sectional view of the non-spherical resin particle taken normal to the direction in which a minimum projected area is produced.

DESCRIPTION OF EMBODIMENTS

Non-Spherical Resin Particles

Non-spherical resin particles in accordance with the present invention have a circular outline when viewed from a direction in which a maximum projected area is produced and a non-circular outline when viewed from a direction in which a minimum projected area is produced, each of the non-spherical resin particles containing a first resin component and a second resin component which is a different type of resin from the first resin component, with the second resin component residing locally near the surface of the particle.

"Non-spherical" refers to the shape of a partly missing sphere. Preferably at least a part (more preferably, more than half) of the surface of the missing part of a non-spherical resin particle is formed of the second resin component, with the rest of the surface of the non-spherical resin particle being formed of the first resin component. The non-spherical shape, or the shape of a partly missing sphere, may, for example, be semi-spherical or biconvex lens-shaped (like Weiqi or Go game stones), resemble a mushroom, or have a horseshoe-like, concave cross-section.

The second resin component preferably integrally resides locally near the non-spherical part of the surface (part of the surface that does not make up the spherical part of the surface) of the non-spherical resin particles.

Non-Spherical Resin Particles with Horseshoe-Like Cross-Section

Figure 1:
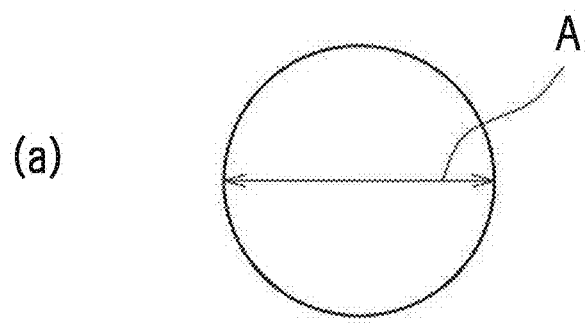
FIGS. 1(a) to 1(c) are illustrations of a non-spherical resin particle with a horseshoe-like cross-section in accordance with an example of the present invention.
Figure 1:
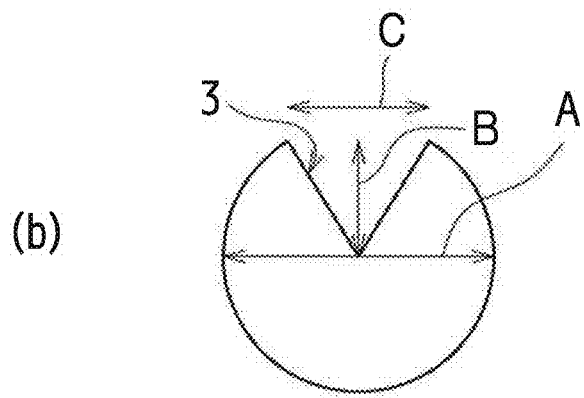
Figure 1:
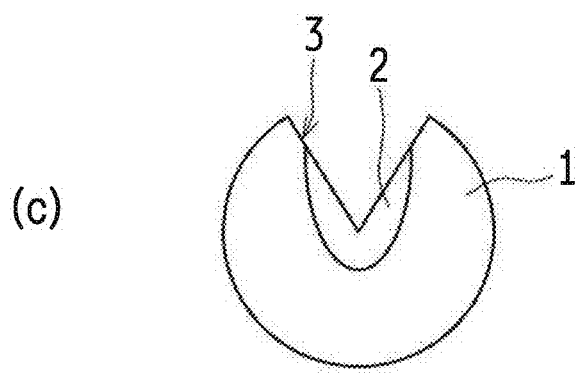

Non-spherical resin particles with a horseshoe-like cross-section in accordance with an example of the present invention, as shown in FIGS. 1(*a*) and 1(*b*), have a circular outline when viewed from a direction in which a maximum projected area is produced and a horseshoe-like outline (a circular sector and the concave in the projection of a notch section 3 (detailed later)) when viewed from a direction in which a minimum projected area is produced. Each of the non-spherical resin particles, as illustrated in FIG. 1(*c*), contains a first and a second resin component 1 and 2 that are different from each other, with the second resin component 2 residing locally near the surface of the non-spherical resin particle.

The non-spherical resin particle, as shown in FIGS. 1(*b*) and 1(*c*), has a partly missing sphere shape and has a single notch section 3 that extends through the particle along its diameter. In the non-spherical resin particle, as illustrated in FIG. 1(*c*), more than half of the surface of the notch section 3 (missing part) is formed of the second resin component 2, and the remaining surface of the non-spherical resin particle is formed of the first resin component 1. The second resin component 2 integrally resides locally near the surface of the notch section 3 (non-spherical part of the particle surface).

The non-spherical resin particle is capable of selectively adsorbing and holding a specific component that has high affinity with the second resin component 2 on the surface of the notch section 3.

The notch section 3 has a depth B (depth of the concave in the projection of the notch section 3). The depth B is preferably 0.1 to 0.9 times, more preferably 0.2 to 0.5 times, and even more preferably 0.3 to 0.45 times the particle diameter (major axis) A of the non-spherical resin particle. If the depth B of the notch section 3 is less than 0.1 times the particle diameter A, the shape-anisotropy is too low to appreciably improve light diffusion, light reflection, and other related properties. On the other hand, if the depth B of the notch section 3 is greater than 0.9 times the particle diameter A, the particle is difficult to manufacture.

The notch section 3 has an opening width C, which is preferably 0.1 to 0.95 times, more preferably 0.4 to 0.7 times, and even more preferably 0.45 to 0.55 times the particle diameter A. If the opening width C of the notch section 3 is less than 0.1 times the particle diameter A, the non-spherical resin particle is too spherical, hence has too low shape-anisotropy, to appreciably improve light diffusion, light reflection, and other related properties. On the other hand, if the opening width C of the notch section 3 is greater than 0.95 times the particle diameter A, the non-spherical resin particle is so semi-spherical that the notch section 3 fails to sufficiently deliver its effect of making the particle selectively adsorb and hold a specific component.

The non-spherical resin particles with a horseshoe-like cross-section are readily obtainable by the manufacturing method of the present invention (detailed later) if the notch section 3 has a depth B in the range of 0.1 to 0.9 times the particle diameter A and an opening width C in the range of 0.1 to 0.95 times the particle diameter A.

Non-Spherical Resin Particles with Mushroom Shape

Figure 2:
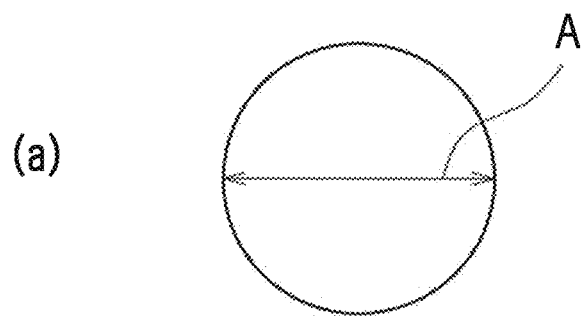
FIGS. 2(a) to 2(c) are illustrations of a non-spherical resin particle with a mushroom shape in accordance with an example of the present invention.
Figure 2:
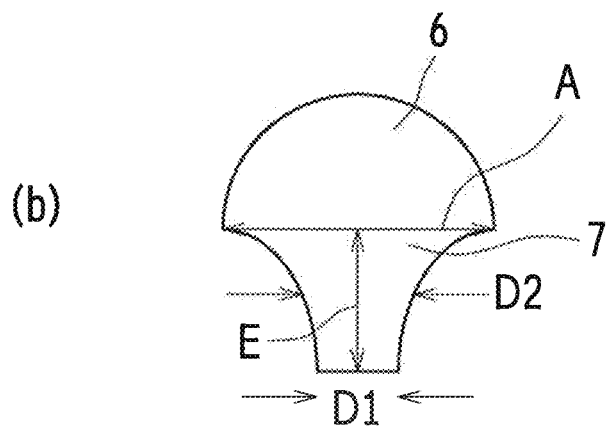
Figure 2:
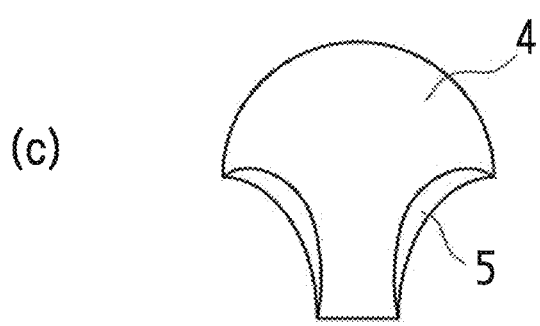

Non-spherical resin particles with a mushroom shape in accordance with an example of the present invention, as shown in FIGS. 2(*a*) and 2(*b*), have a circular outline when viewed from a direction in which a maximum projected area is produced and a non-circular outline when viewed from a direction in which a minimum projected area is produced. Each of the non-spherical resin particles, as illustrated in FIG. 2(*c*), contains a first and a second resin component 4 and 5 that are different from each other, with the second resin component 5 residing locally near the surface of the non-spherical resin particle.

The non-spherical resin particle, as shown in FIGS. 2(*b*) and 2(*c*), has a partly missing sphere shape and has a semi-spherical cap section 6 and a stem section 7 shaped like a partly missing semi-sphere. In the non-spherical resin particle, as illustrated in FIG. 2(*c*), more than half of the surface of the stem section 7 (missing part) is formed of the second resin component 5, and the rest of the surface of the non-spherical resin particle is formed of the first resin component 4. The second resin component 5 integrally resides locally near the surface of the stem section 7 (non-spherical part of the particle surface).

The far end (bottom) of the stem section 7 has a width D1. The width D1 is preferably 0.1 to 0.8 times, more preferably 0.15 to 0.6 times, and even more preferably 0.25 to 0.45 times the particle diameter (major axis) A of the non-spherical resin particle. If the width D1 of the far end of the stem section 7 is less than 0.1 times the particle diameter A, the non-spherical resin particle is so semi-spherical that the mushroom shape fails to sufficiently deliver its unique effect. On the other hand, if the width D1 of the far end of the stem section 7 is greater than 0.8 times the particle diameter A, the non-spherical resin particle is too spherical, hence has too low shape-anisotropy, to appreciably improve light diffusion, light reflection, and other related properties.

The mid-portion of the stem section 7 (part of the stem section 7 that is between its end and base) has a width D2. The width D2 is preferably 0.2 to 0.9 times, more preferably 0.3 to 0.7 times, and even more preferably 0.45 to 0.6 times the particle diameter A of the non-spherical resin particle. If the width D2 of the mid-portion of the stem section 7 is less than 0.2 times the particle diameter A, the non-spherical resin particle is so semi-spherical that the mushroom shape fails to sufficiently deliver its unique effect. On the other hand, if the width D2 of the mid-portion of the stem section 7 is greater than 0.9 times the particle diameter A, the non-spherical resin particle is too spherical, hence has too low shape-anisotropy, to appreciably improve light diffusion, light reflection, and other related properties.

The stem section 7 has a height E as measured in the stem direction. The height E is preferably 0.2 to 1.5 times, more preferably 0.2 to 0.7 times, and even more preferably 0.2 to 0.6 times the particle diameter A of the non-spherical resin particle. If the height E of the stem section 7 as measured in the stem direction is less than 0.2 times the particle diameter A, the non-spherical resin particle is so semi-spherical that the mushroom shape fails to sufficiently deliver its unique effect. On the other hand, if the height E of the stem section 7 as measured in the stem direction is greater than 1.5 times the particle diameter A, the particle is difficult to manufacture.

The non-spherical resin particles with a mushroom shape are readily obtainable by the manufacturing method of the present invention (detailed later) if the width D1 of the far end of the stem section 7 is 0.1 to 0.8 times the particle diameter A, the width D2 of the mid-portion of the stem section 7 is 0.2 to 0.9 times the particle diameter A, and the height E of the stem section 7 as measured in the stem direction is 0.2 to 1.5 times the particle diameter A.

Non-Spherical (Semi-Spherical) Resin Particles

Figure 3:
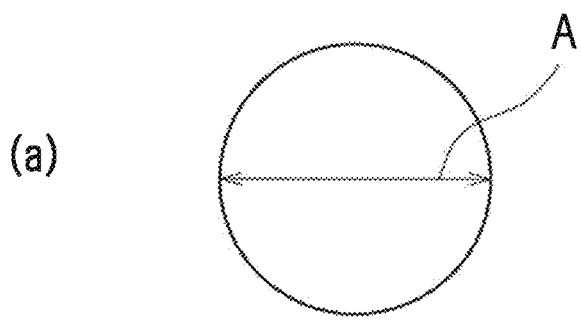
FIGS. 3(a) to 3(c) are illustrations of a non-spherical (semi-spherical) resin particle in accordance with an example of the present invention.
Figure 3:
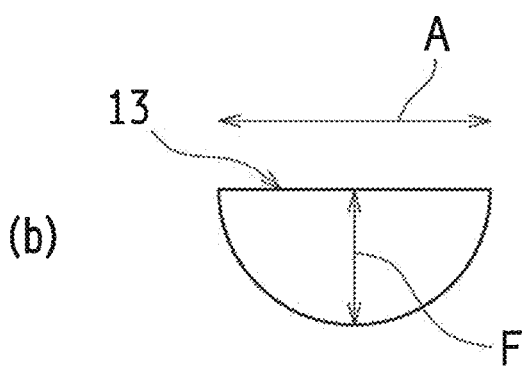
Figure 3:
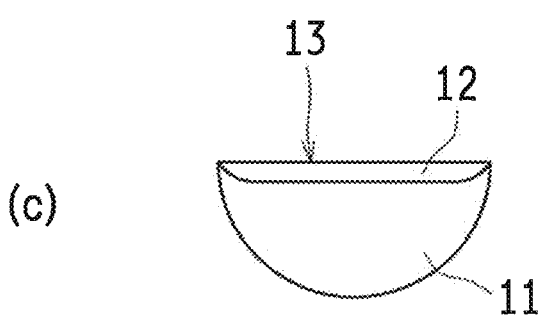

Non-spherical (semi-spherical) resin particles in accordance with an example of the present invention, as shown in FIGS. 3(*a*) and 3(*b*), have a circular outline when viewed from a direction in which a maximum projected area is produced and a semicircular outline when viewed from a direction in which a minimum projected area is produced. Each of the non-spherical resin particles, as illustrated in FIG. 3(*c*), contains a first and a second resin component 11 and 12 that are different from each other, with the second resin component 12 residing locally near the surface of the non-spherical resin particle.

The non-spherical resin particle, as shown in FIGS. 3(*b*) and 3(*c*), is shaped like a half-missing sphere and has a plane portion 13 for the missing half of the sphere. In the non-spherical resin particle, as illustrated in FIG. 3(*c*), the substantially entire surface of the plane portion 13 (missing part) is formed of the second resin component 12, and the rest of the surface of the non-spherical resin particle is formed of the first resin component 11. The second resin component 12 integrally resides locally near the surface of the plane portion 13 (non-spherical part of the particle surface).

The non-spherical resin particle has a minor axis F (height as measured in the direction in which a maximum projected area is produced in FIG. 3(*b*)). The minor axis F is preferably 0.2 to 0.8 times, more preferably 0.4 to 0.7 times, and even more preferably 0.5 to 0.6 times the particle diameter (major axis) A of the non-spherical resin particle. If the minor axis F is less than 0.2 times the particle diameter A, the particle is difficult to manufacture. On the other hand, if the minor axis F is greater than 0.8 times the particle diameter A, the non-spherical resin particle is too spherical, hence has too low shape-anisotropy, to appreciably improve light diffusion, light reflection, and other related properties.

The non-spherical (semi-spherical) resin particles are readily obtainable by the manufacturing method of the present invention (detailed later) if the minor axis F is 0.2 to 0.8 times the particle diameter A.

Non-Spherical (Biconvex Lens-Shaped) Resin Particles

Figure 4:
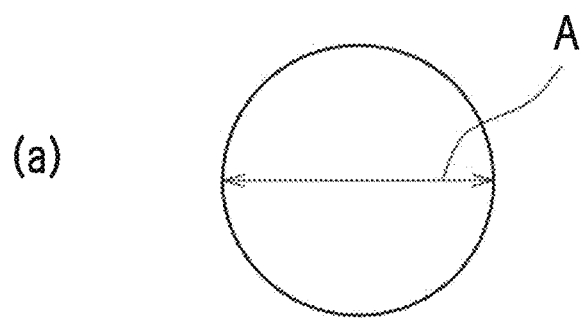
FIGS. 4(a) to 4(c) are illustrations of a non-spherical (bi-convex lens-shaped) resin particle in accordance with an example of the present invention.
Figure 4:
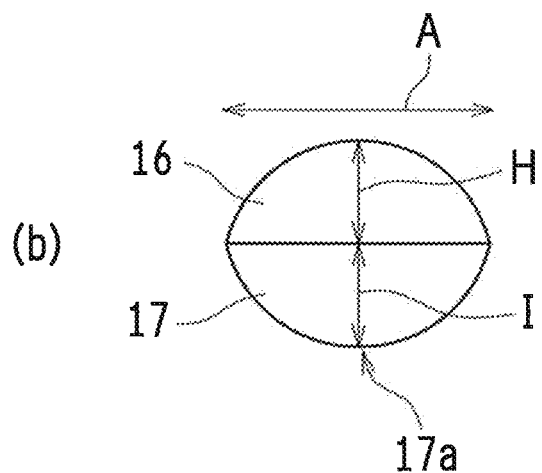
Figure 4:
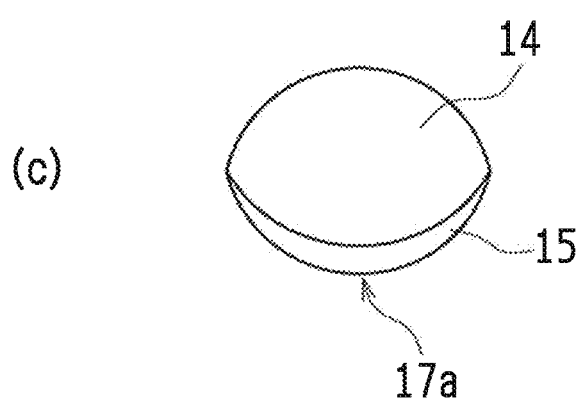

The non-spherical (biconvex lens-shaped) resin particles in accordance with an example of the present invention, as shown in FIGS. 4(*a*) and 4(*b*), have a circular outline when viewed from a direction in which a maximum projected area is produced and a non-circular outline when viewed from a direction in which a minimum projected area is produced. Each of the non-spherical resin particles, as illustrated in FIG. 4(*c*), contains a first and a second resin component 14 and 15 that are different from each other, with the second resin component 15 residing locally near the surface of the non-spherical resin particle.

The non-spherical resin particle, as shown in FIGS. 4(*b*) and 4(*c*), has a partly missing sphere shape and composed of two planoconvex lens-shaped sections 16 and 17, with the plane portion of the planoconvex lens-shaped section 16 being joined to the plane portion of the planoconvex lens-shaped section 17. Each planoconvex lens-shaped section 16 and 17 has the shape of the smaller one of two fragments obtained by dividing a sphere by a plane that does not include the center of the sphere. The planoconvex lens-shaped section 16 has a height H as measured in a direction in which a maximum projected area is produced. The planoconvex lens-shaped section 17 has a height I as measured in a direction in which a maximum projected area is produced. The height H may be equal to the height I and is preferably greater than the height I. In the non-spherical resin particle, as illustrated in FIG. 4(c), the substantially entire surface 17a of the planoconvex lens-shaped section 17 (typically, the smaller one of planoconvex lens-shaped sections) is formed of the second resin component 15, and the rest of the surface of the non-spherical resin particle is formed of the first resin component 14. The second resin component 15 integrally resides locally near the surface of the planoconvex lens-shaped section 17 (non-spherical part of the particle surface).

The height H is preferably 0.2 to 0.8 times, more preferably 0.2 to 0.7 times, and even more preferably 0.35 to 0.55 times the particle diameter (major axis) A of the non-spherical resin particle. If the height H is less than 0.2 times the particle diameter A or greater than 0.8 times the particle diameter A, the particle is difficult to manufacture.

The height I is preferably 0.1 to 0.8 times, more preferably 0.1 to 0.5 times, and even more preferably 0.1 to 0.3 times the particle diameter A. If the height I is less than 0.1 times the particle diameter A, the non-spherical resin particle is so semi-spherical that the biconvex lens shape fails to sufficiently deliver its unique effect. On the other hand, if the height I is greater than 0.8 times the particle diameter A, the particle is difficult to manufacture. In addition, if the height I is greater than 0.3 times the particle diameter A, the non-spherical resin particle is too spherical, hence has too low shape-anisotropy, to appreciably improve light diffusion, light reflection, and other related properties.

The non-spherical (biconvex lens-shaped) resin particles are readily obtainable by the manufacturing method of the present invention (detailed later) if the height H is 0.2 to 0.8 times the particle diameter A, and the height H is 0.1 to 0.8 times the particle diameter A.

In the non-spherical resin particles shown in FIGS. 1 to 4, the particle diameter A is preferably from 0.5 to 50 µm. FIGS. 1 to 4 are mere illustrations of ideal shapes and included here for the purpose of description of the shapes of non-spherical resin particles. Actual non-spherical resin particles may have a bulge or recess and are still encompassed within the scope of the present invention.

Sphere-Equivalent Volume-Average Particle Diameter of Non-Spherical Resin Particles The non-spherical resin particles in accordance with the present invention preferably have an average particle diameter of 0.5 to 50 µm when calculated from an equivalent spherical volume ("sphere-equivalent volume-average particle diameter"). When this is actually the case, the particles are suited for various uses. If the non-spherical resin particles in accordance with the present invention are to be used as an element (light diffusion agent) for an anti-glare film, the particles more preferably have a sphere-equivalent volume-average particle diameter of 1.5 to 8 µm. When this is actually the case, the resultant anti-glare film exhibits good anti-glare properties. If the non-spherical resin particles in accordance with the present invention are to be used as an element (light diffusion agent) for a light diffuser, the particles more preferably have a sphere-equivalent volume-average particle diameter of 1 to 50 µm, and even more preferably 1 to 10 µm. When this is actually the case, the resultant light diffuser exhibits good light diffusion properties. If the non-spherical resin particles in accordance with the present invention are to be used as an ingredient for an external preparation, the particles preferably have a sphere-equivalent volume-average particle diameter of 1 to 50 µm. When this is actually the case, the resultant external preparation is of good quality. If the non-spherical resin particles in accordance with the present invention are to be used as a paper coating agent, the particles preferably have a sphere-equivalent volume-average particle diameter of 0.5 to 10 µm. When this is actually the case, the resultant paper coating agent is of good quality. If the sphere-equivalent volume-average particle diameter is 1 to 10 µm, the non-spherical resin particles arranged as above are easy to control in terms of their shape and easy to manufacture, to obtain a desired non-spherical shape.

Hydrophilic Resin

In the non-spherical resin particles in accordance with the present invention, the first resin component is preferably a hydrophilic resin. The hydrophilic resin is preferably a resin containing at least one type of hydrophilic substituent selected from the group consisting of a hydroxyl group, a carboxyl group, a sulfo group, and an amino group. The resin with a hydrophilic substituent is obtained by, for example, homopolymerization or copolymerization of a vinyl-based polymerizable monomer containing at least one type of hydrophilic substituent selected from the group consisting of a hydroxyl group, a carboxyl group, a sulfo group, and an amino group. A vinyl-based polymerizable monomer is a compound with at least one polymerizable alkenyl group (vinyl group in a broader sense of the term) per molecule. The vinyl-based polymerizable monomer with a hydrophilic substituent may be, for example, a (meth)acrylic acid derivative, such as (meth)acrylic acid, (meth)acrylamide, 2-hydroxylethyl(meth)acrylate, and a (meth)acrylic acid ester with an alkylene oxide group including a hydroxyl group.

Alternatively, the hydrophilic resin is preferably a resin obtainable by homopolymerization or copolymerization of a vinyl-based polymerizable monomer that exhibits a solubility of 1 wt % or greater in 20° C. water. The vinyl-based polymerizable monomer that exhibits a solubility of 1 wt % or greater in 20° C. water may be, for example, a (meth)acrylic acid derivative, such as a (meth)acrylic acid ester with an alkylene oxide group including no hydroxyl group, methyl (meth)acrylate, ethyl(meth)acrylate, glycidyl(meth)acrylate, or acrylonitrile; or a vinyl acetate, as well as those compounds given as examples of the vinyl-based polymerizable monomer with a hydrophilic substituent ((meth)acrylic acid, (meth)acrylamide, 2-hydroxylethyl(meth)acrylate, and a (meth)acrylic acid ester with an alkylene oxide group including a hydroxyl group).

Preferred among these vinyl-based polymerizable monomers are a (meth)acrylic acid ester with an alkylene oxide group including a hydroxyl group and a (meth)acrylic acid ester with an alkylene oxide group including no hydroxyl group, because these compounds facilitate the manufacture of non-spherical resin particles with the non-spherical shape and non-uniform component distribution that are unique to the present invention. Examples of such a (meth)acrylic acid ester with an alkylene oxide group including a hydroxyl group and (meth)acrylic acid ester with an alkylene oxide group including no hydroxyl group include compounds of general formula (1) below.

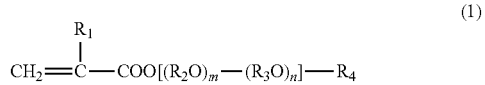

(1)

In general formula (1), $R_1$ is either H or $CH_3$, $R_2$ and $R_3$ are different $C_2$-$C_5$ alkylene groups ($C_2H_4$, $C_3H_6$, $C_4H_8$, or $C_5H_{10}$), m and n are numbers from 0 to 50, at least either m or n being not 0, and $R_4$ is either H or $CH_3$. If m is greater than 50 or if n is greater than 50, the monomers of general formula (1) may exhibit decreased polymerization stability during polymerization and stick together. In general formula (1), m and n are preferably from 0 to 30 and more preferably from 0 to 15. Preferred among the compounds of general formula (1) are, for example, poly(ethylene glycol-propylene glycol) monomethacrylates, polypropylene glycol monomethacrylates, and methoxypolyethylene glycol monomethacrylates.

The (meth)acrylic acid ester with an alkylene oxide group including a hydroxyl group and the (meth)acrylic acid ester with an alkylene oxide group including no hydroxyl group may be a commercial product. An example of such a commercial product is a Blemmer® series manufactured by NOF Corporation. Especially preferred in the Blemmer® series are, for example, Blemmer® 50 PEP-300, which is a poly (ethylene glycol-propylene glycol)monomethacrylate (a mixture of compounds of general formula (1), where $R_1$ is $CH_3$, $R_2$ is $C_2H_4$, $R_3$ is $C_3H_6$, m is 3.5 on average, n is 2.5 on average, and $R_4$ is H), Blemmer® 70 PEP-350B, which is a poly(ethylene glycol-propylene glycol)monomethacrylate (a mixture of compounds of general formula (1), where $R_1$ is $CH_3$, $R_2$ is $C_2H_4$, $R_3$ is $C_3H_6$, m is 5 on average, n is 2 on average, and $R_4$ is H), Blemmer® PP-1000, which is a polypropylene glycol monomethacrylate (a mixture of compounds of general formula (1), where $R_1$ is $CH_3$, $R_3$ is $C_3H_6$, m is 0, n is 4 to 6 on average, and $R_4$ is H), and Blemmer® PME-400, which is a methoxypolyethylene glycol monomethacrylate (a mixture of compounds of general formula (1), where $R_1$ is $CH_3$, $R_2$ is $C_2H_4$, m is 9 on average, n is 0, and $R_4$ is $CH_3$). Any one of these vinyl-based polymerizable monomers may be used alone, or two or more of them may be mixed for use.

Hydrophobic Resin

In the non-spherical resin particles in accordance with the present invention, the second resin component is preferably a hydrophobic resin. The hydrophobic resin is preferably a resin with a halogenated alkyl group, such as an alkyl fluoride group, an alkyl chloride group, an alkyl bromide group, or an alkyl iodide group or a resin with an alicyclic hydrocarbon group, such as a cyclohexyl group. The resin with a halogenated alkyl group is obtained by homopolymerization or copolymerization of a vinyl-based polymerizable monomer containing a halogenated alkyl group. The vinyl-based polymerizable monomer with a halogenated alkyl group may be, for example, a (meth)acrylic acid ester having a $C_2$-$C_{10}$ alkyl fluoride group in an ester moiety thereof, such as trifluoromethyl methacrylate, 2,2,2-trifluoroethyl acrylate, 2,2,2-trifluoroethyl methacrylate, 2,2,3,3-tetrafluoropropyl acrylate, 2,2,3,3-tetrafluoropropyl methacrylate, 2,2,3,4,4,4-hexafluorobutyl methacrylate, 1H,1H,5H-octafluoropentyl acrylate, 1H,1H,5H-octafluoropentyl methacrylate, perfluoroctylethyl methacrylate, or perfluoroctylethyl acrylate. The resin with an alicyclic hydrocarbon group is obtained by homopolymerization or copolymerization of a vinyl-based polymerizable monomer containing an alicyclic hydrocarbon group. The vinyl-based polymerizable monomer with an alicyclic hydrocarbon group may be, for example, a (meth)acrylic acid ester having an alicyclic hydrocarbon group in an ester moiety thereof, such as cyclohexyl(meth)acrylate or isobornyl(meth) acrylate. Any one of these vinyl-based polymerizable monomers may be used alone, or two or more of them may be mixed for use.

The vinyl-based polymerizable monomer with a halogenated alkyl group is preferably a vinyl-based polymerizable monomer with an alkyl fluoride group. When this is actually the case, the resultant non-spherical resin particles are likely to have a low refractive index and a high transparency. The vinyl-based polymerizable monomer with a halogenated alkyl group is preferably a (meth)acrylic acid ester having a $C_2$-$C_{10}$ halogenated alkyl group in an ester moiety thereof and more preferably a (meth)acrylic acid ester having a $C_2$-$C_{10}$ alkyl fluoride group in an ester moiety thereof. When this is actually the case, the polymer produced from the monomer mixture is likely to phase-separate from the resin particles during the polymerization of the monomer mixture. That facilitates achieving the non-spherical shape and non-uniform component distribution that are unique to the present invention. The number of halogen atoms in the halogenated alkyl group is preferably at least 40% and more preferably at least 50% the total number of hydrogen atoms in a corresponding alkyl group. When this is actually the case, the polymer produced from the monomer mixture is likely to phase-separate from the resin particles during the polymerization of the monomer mixture. That facilitates achieving the non-spherical shape and non-uniform component distribution that are unique to the present invention. For example, for a 2,2,2-trifluoroethyl group, the total number of hydrogen atoms is 5, and the number of halogen atoms is 3 in the corresponding alkyl group. Hence, it follows that 60% of the hydrogen atoms in the corresponding alkyl group are replaced by halogen atoms.

Method of Manufacturing Non-Spherical Resin Particles

The method of manufacturing non-spherical resin particles in accordance with the present invention involves either allowing particles of a resin to absorb a vinyl-based polymerizable monomer contained in an aqueous emulsion and polymerizing the absorbed vinyl-based polymerizable monomer or dissolving a resin in a vinyl-based polymerizable monomer to prepare a solution and polymerizing the solution in an aqueous medium, wherein the resin has a moiety derived from a (meth)acrylic acid ester having a $C_2$-$C_{10}$ halogenated alkyl group or alicyclic hydrocarbon group in an ester moiety thereof and has a weight-average molecular weight of from 150,000 to 1,000,000 as measured by gel permeation chromatography, and the vinyl-based polymerizable monomer contains a crosslinking monomer in an amount of 5 to 50 wt % as based on a total amount of the vinyl-based polymerizable monomer. This method is capable of manufacturing the non-spherical resin particles in accordance with the present invention in a highly reliable manner.

Method of Manufacturing Non-Spherical Resin Particles by Seed Polymerization

First will be described one of methods of manufacturing non-spherical resin particles in accordance with the present invention: specifically, a method of manufacturing non-spherical resin particles by seed polymerization that involves allowing resin particles to absorb a vinyl-based polymerizable monomer contained in an aqueous emulsion and polymerizing the absorbed vinyl-based polymerizable monomer.

The method of manufacturing non-spherical resin particles by seed polymerization includes: a resin particle preparation step of polymerizing a vinyl-based polymerizable monomer (hereinafter, "hydrophobic monomer") containing a (meth) acrylic acid ester having in an ester moiety thereof a $C_2$-$C_{10}$ halogenated alkyl group or alicyclic hydrocarbon group, to produce resin particles having a weight-average molecular weight of from 150,000 to 1,000,000 as measured by gel permeation chromatography; and a seed polymerization step of allowing the resin particles obtained in the resin particle preparation step to absorb a vinyl-based polymerizable monomer (hereinafter, "monomer mixture") contained in an aqueous emulsion containing a crosslinking monomer in an amount of 5 to 50 wt % as based on the total amount of the vinyl-based polymerizable monomer and polymerizing the absorbed monomer mixture.

Resin Particle Preparation Step

In the resin particle preparation step, resin particles are obtained by polymerizing a hydrophobic monomer containing a (meth)acrylic acid ester having in an ester moiety thereof a $C_2$-$C_{10}$ halogenated alkyl group or alicyclic hydrocarbon group.

The (meth)acrylic acid ester having a $C_2$-$C_{10}$ halogenated alkyl group or alicyclic hydrocarbon group in an ester moiety thereof may be, for example, one of the various (meth)acrylic acid esters having a $C_2$-$C_{10}$ halogenated alkyl group in an ester moiety thereof or one of the various (meth)acrylic acid esters having an alicyclic hydrocarbon group in an ester moiety thereof, which are given as examples under the heading "Hydrophobic resin" above.

The (meth)acrylic acid ester having a $C_2$-$C_{10}$ halogenated alkyl group or alicyclic hydrocarbon group in an ester moiety thereof is used in an amount of preferably at least 50 wt % and more preferably at least 80 wt % as based on the total amount of the hydrophobic monomer. When this is actually the case, after the resin particles are allowed to absorb the monomer mixture in the seed polymerization step, the polymer produced from the monomer mixture is likely to phase-separate from the resin particles during the polymerization of the monomer mixture. That facilitates achieving the non-spherical shape and non-uniform component distribution that are unique to the present invention.

The hydrophobic monomer may contain a vinyl-based polymerizable monomer other than the (meth)acrylic acid ester having a $C_2$-$C_{10}$ halogenated alkyl group or alicyclic hydrocarbon group in an ester moiety thereof. The other vinyl-based polymerizable monomer is preferably a monofunctional (meth)acrylic acid ester ((meth)acrylic acid ester having only one polymerizable alkenyl group per molecule) other than the (meth)acrylic acid ester having a $C_2$-$C_{10}$ halogenated alkyl group or alicyclic hydrocarbon group in an ester moiety thereof. The monofunctional (meth)acrylic acid ester may be, for example, methyl(meth)acrylate, ethyl(meth)acrylate, n-propyl(meth)acrylate, isopropyl(meth)acrylate, n-butyl(meth)acrylate, isobutyl(meth)acrylate, tert-butyl (meth)acrylate, n-pentyl(meth)acrylate, n-hexyl(meth)acrylate, n-heptyl(meth)acrylate, n-octyl(meth)acrylate, 2-ethyl hexyl(meth)acrylate, n-nonyl(meth)acrylate, and n-decyl (meth)acrylate. Any one of these compounds may be used alone, or two or more of them may be mixed for use.

The hydrophobic monomer preferably does not contain a crosslinking monomer (a compound having two or more polymerizable alkenyl groups per molecule). If the hydrophobic monomer contains a crosslinking monomer, the resultant non-spherical resin particles have low non-sphericity, reducing the effect of the non-spherical shape that is unique to the present invention.

The hydrophobic monomer may be polymerized in the presence of a molecular weight modifier. The molecular weight modifier may be, for example, a mercaptan, such as n-octyl mercaptan, n-dodecyl mercaptan, or tert-dodecyl mercaptan; an α-methyl styrene dimer; a terpene, such as γ-terpinene or dipentene; or a chain transfer agent, such as chloroform, carbon tetrachloride, or a like halogenated hydrocarbon. The molecular weight modifier is preferably a mercaptan. The molecular weight modifier may be used in such an amount that the resultant resin particles have a weight-average molecular weight of from 150,000 to 1,000, 000. The molecular weight modifier is used in an amount of preferably 0.1 to 10 parts by weight, more preferably 0.1 to 0.9 parts by weight, and even more preferably 0.1 to 0.5 parts by weight as based on 100 parts by weight of the hydrophobic monomer. That further facilitates achieving the non-spherical shape and non-uniform component distribution that are unique to the present invention.

The resin particles may have a weight-average molecular weight of from 150,000 to 1,000,000 and preferably have a weight-average molecular weight of from 200,000 to 800,000, both as measured by GPC (gel permeation chromatography). If the resin particles have a weight-average molecular weight of 150,000 or less, the polymer produced from the monomer mixture is unlikely to phase-separate from the resin particles during the polymerization of the monomer mixture. That makes it difficult to achieve the non-spherical shape and non-uniform component distribution that are unique to the present invention. On the other hand, if the resin particles have a weight-average molecular weight of greater than 1,000,000, the non-spherical shape and non-uniform component distribution that are unique to the present invention become difficult to achieve. Spherical resin particles may contaminate the resultant non-spherical resin particles. In other words, if the weight-average molecular weight is greater than 1,000,000, the resin particles absorb less of the monomer. Without having absorbed the monomer mixture, the monomer polymerizes alone and forms spherical resin particles that are different from the non-spherical resin particles in accordance with the present invention.

The hydrophobic monomer may be polymerized, for example, by emulsion polymerization (including soap-free emulsion polymerization), suspension polymerization, or a like publicly known method. In view of the uniformity of the particle diameters of the resultant resin particles and the simplicity and convenience of the manufacture, emulsion polymerization is preferred. The following will describe an emulsion polymerization-based method, which is however for illustrative purposes only.

To emulsion-polymerize the hydrophobic monomer, first, the hydrophobic monomer is dispersed in an aqueous medium to prepare an aqueous emulsion.

The aqueous medium may be, for example, water or a mixed medium of water and a water-soluble solvent (e.g., lower alcohol (alcohol containing 5 or less carbon atoms)). The surfactants detailed later under the heading "Seed polymerization step" may or may not be added to the aqueous medium. The hydrophobic monomer is added to the aqueous medium and dispersed in the aqueous medium with a fine emulsifier, such as a main stirrer, a homogenizer, an ultrasonic processor, or a nanomizer, to prepare an aqueous emulsion which is then heated to a polymerization temperature. After the reaction system is purged (filled) with nitrogen or a like inert gas, polymerization is carried out while adding dropwise a polymerization initiator dissolved in water to the dispersion liquid, to obtain resin particles.

The polymerization initiator may be, for example, a persulfate, such as potassium persulfate, ammonium persulfate, or sodium persulfate; an organic peroxide, such as benzoyl peroxide, lauroyl peroxide, orthochlorobenzoyl peroxide, orthomethoxybenzoyl peroxide, 3,5,5-trimethylhexanoyl peroxide, tert-butyl peroxy-2-ethylhexanoate, or di-tert-butyl peroxide; or an azo-based compound, such as 2,2'-azobisisobutyronitrile, 1,1'-azobiscyclohexane carbonitrile, or 2,2'-azobis(2,4-dimethyl valeronitrile). The polymerization initiator is used preferably in an amount of 0.1 to 3 parts by weight as based on 100 parts by weight of the hydrophobic monomer.

Next, the hydrophobic monomer contained in an aqueous emulsion is polymerized to obtain resin particles. The polymerization temperature may be suitably selected according to the type of the hydrophobic monomer and the type of the polymerization initiator. The polymerization temperature is preferably from 25 to 110° C. and more preferably from 50 to 100° C. After the polymerization is complete, if necessary, the resin particles may be filtered out or otherwise separated out from the aqueous medium, residual aqueous medium may be further removed from the resin particles by, for example, centrifugation, and the resultant resin particles may be washed in water and a solvent and subsequently dried.

Thus, hydrophobic resin particles are obtained that have a moiety derived from a (meth)acrylic acid ester having in an ester moiety thereof a $C_2$-$C_{10}$ halogenated alkyl group or alicyclic hydrocarbon group.

The hydrophobic monomer may be polymerized in the presence of a polymer of a (meth)acrylic acid ester. Next will be described a method of polymerizing the hydrophobic monomer in the presence of a polymer of a (meth)acrylic acid ester.

A polymer of a (meth)acrylic acid ester is used in an amount of preferably 100 parts by weight or less and more preferably from 1 to 80 parts by weight as based on 100 parts by weight of the hydrophobic monomer. If a polymer of a (meth)acrylic acid ester is used in an amount of 100 parts by weight or less as based on 100 parts by weight of the hydrophobic monomer, the polymer produced from the monomer mixture is likely to phase-separate from the resin particles during the polymerization of the monomer mixture. That facilitates achieving the non-spherical shape and non-uniform component distribution that are unique to the present invention. Besides, the particles sufficiently grow in diameter during the polymerization, improving productivity. On the other hand, if a polymer of a (meth)acrylic acid ester is used in an amount of 1 part by weight or more as based on 100 parts by weight of the hydrophobic monomer, the hydrophobic monomer suspension-polymerizes alone in the aqueous medium without being absorbed by the polymer of the (meth)acrylic acid ester, which prevents improper particles from forming.

When that is actually the case, after a (meth)acrylic acid ester is polymerized to obtain (meth)acrylic acid ester polymer particles, a seed polymerization method is preferably used whereby the (meth)acrylic acid ester polymer particles are allowed to absorb the hydrophobic monomer and subsequently polymerized. In other words, in the resin particle preparation step, the resin particles are preferably prepared by two sub-steps: a first sub-step of polymerizing a (meth) acrylic acid ester to obtain (meth)acrylic acid ester polymer particles and a second sub-step of allowing the (meth)acrylic acid ester polymer particles to absorb the hydrophobic monomer and subsequently polymerizing the hydrophobic monomer. When this is actually the case, non-spherical resin particles are likely to be obtained with the non-spherical shape and non-uniform component distribution that are unique to the present invention in the seed polymerization step (detailed later). It will be described later in detail how the (meth)acrylic acid ester polymer particles are manufactured.

According to the seed polymerization method, first, the hydrophobic monomer is dispersed in an aqueous medium to prepare an aqueous emulsion, and (meth)acrylic acid ester polymer particles are added to the aqueous emulsion as seed particles. The aqueous medium may be, for example, any one of the aforementioned media. The surfactants detailed later under the heading "Seed polymerization step" may be added to the aqueous medium. Besides, as mentioned earlier, the hydrophobic monomer may be polymerized in the presence of a molecular weight modifier.

The hydrophobic monomer may be mixed with an aforementioned polymerization initiator if necessary, in which case the polymerization initiator is preferably used in the aforementioned amounts. The polymerization initiator may be mixed with the hydrophobic monomer before being dispersed in the aqueous medium. Alternatively, the polymerization initiator and the hydrophobic monomer may be separately dispersed in aqueous media before being mixed together. The droplets of the hydrophobic monomer contained in the resultant aqueous emulsion preferably have smaller particle diameters than the (meth)acrylic acid ester polymer particles so that the hydrophobic monomer can be efficiently absorbed by the (meth)acrylic acid ester polymer particles.

The (meth)acrylic acid ester polymer particles may be added to the aqueous emulsion either directly or after being dispersed in an aqueous medium (e.g., added in the form of an aqueous emulsion). If acrylic acid ester polymer particles are added after being dispersed in an aqueous medium, an aqueous emulsion containing the acrylic acid ester polymer particles obtained by emulsion polymerization may be added to an aqueous emulsion containing the hydrophobic monomer. In addition, the acrylic acid ester polymer particles (or the acrylic acid ester polymer particles dispersed in an aqueous medium) may be added to an aqueous medium either at the same time as or before the hydrophobic monomer is dispersed in the aqueous medium. After completing both the addition of the (meth)acrylic acid ester polymer particles to the aqueous medium or emulsion and the preparation of the aqueous emulsion, the (meth)acrylic acid ester polymer particles are allowed to absorb the hydrophobic monomer contained in the aqueous emulsion. The absorption can be generally carried out by stirring at room temperature (about 20° C.) for 1 to 12 hours the aqueous emulsion to which the (meth)acrylic acid ester polymer particles have been added. The absorption may be accelerated by heating the aqueous emulsion to approximately 30 to 50° C.

The (meth)acrylic acid ester polymer particles swell as they absorb the hydrophobic monomer. The completion of the absorption is determined by observing the growth of the particle diameter under an optical microscope.

Next, the hydrophobic monomer absorbed by the (meth) acrylic acid ester polymer particles are polymerized to obtain resin particles. The polymerization temperature may be suitably selected according to the type of the hydrophobic monomer and the type of the polymerization initiator. The polymerization temperature is preferably from 25 to 110° C. and more preferably from 50 to 100° C. The polymerization reaction is preferably carried out at elevated temperature after the hydrophobic monomer is completely absorbed by the (meth) acrylic acid ester polymer particles. After the polymerization is complete, if necessary, the resin particles may be filtered out or otherwise separated out from the aqueous medium, residual aqueous medium may be further removed from the resin particles by, for example, centrifugation, and the resultant resin particles may be washed in water and a solvent and subsequently dried.

Thus, hydrophobic resin particles that have a moiety derived from a (meth)acrylic acid ester having in an ester moiety thereof a $C_2$-$C_{10}$ halogenated alkyl group or alicyclic hydrocarbon group are obtained by polymerization in the presence of (meth)acrylic acid ester polymer particles. The resin particles are by no means limited in size and shape in any particular manner. The resin particles used are generally spherical and have an average particle diameter of 0.1 to 5 μm.
Method of Manufacturing (Meth)Acrylic Acid Ester Polymer Particles Next will be described a method of manufacturing (meth) acrylic acid ester polymer particles that is used according to a need in the resin particle preparation step.

A (meth)acrylic acid ester is polymerized in the method of manufacturing (meth)acrylic acid ester polymer particles. The (meth)acrylic acid ester may be, for example, methyl (meth)acrylate, ethyl(meth)acrylate, n-propyl(meth)acrylate, isopropyl(meth)acrylate, n-butyl(meth)acrylate, isobutyl (meth)acrylate, tert-butyl(meth)acrylate, n-pentyl(meth) acrylate, n-hexyl(meth)acrylate, n-heptyl(meth)acrylate, n-octyl(meth)acrylate, 2-ethyl hexyl(meth)acrylate, n-nonyl (meth)acrylate, n-decyl(meth)acrylate, or one of the various compounds given as examples of the (meth)acrylic acid ester having a $C_2$-$C_{10}$ halogenated alkyl group or alicyclic hydrocarbon group in an ester moiety thereof. Any one of these compounds may be used alone, or two or more of them may be mixed for use. The (meth)acrylic acid ester may have the same composition as the hydrophobic monomer.

The (meth)acrylic acid ester may be polymerized, for example, by emulsion polymerization (including soap-free emulsion polymerization), suspension polymerization, or a like publicly known method. In view of the particle diameter uniformity of the resultant (meth)acrylic acid ester polymer particles and the simplicity and convenience of the manufacture, however, emulsion polymerization is preferred. The following will describe an emulsion polymerization-based method, which is however for illustrative purposes only.

To emulsion-polymerize the (meth)acrylic acid ester to obtain (meth)acrylic acid ester polymer particles, first, the (meth)acrylic acid ester is dispersed in an aqueous medium to prepare an aqueous emulsion. The aqueous medium may be, for example, any one of the aforementioned media. The surfactants detailed later under the heading "Seed polymerization step" may be added to the aqueous medium. The aqueous emulsion may be prepared, for example, by a method using one of the aforementioned fine emulsifiers.

The (meth)acrylic acid ester may be mixed with an aforementioned polymerization initiator if necessary. The polymerization initiator may be mixed with the (meth)acrylic acid ester before being dispersed in the aqueous medium. Alternatively, the polymerization initiator and the (meth)acrylic acid ester may be separately dispersed in aqueous media before being mixed together. The polymerization initiator is used in an amount of preferably 0.1 to 3 parts by weight as based on 100 parts by weight of the (meth)acrylic acid ester.

The (meth)acrylic acid ester is preferably polymerized in the presence of an aforementioned chain transfer agent. The chain transfer agent is preferably a mercaptan. The chain transfer agent is used in an amount of preferably 0.1 to 0.9 parts by weight and more preferably 0.1 to 0.5 parts by weight as based on 100 parts by weight of the (meth)acrylic acid ester. When this is actually the case, the polymer produced from the monomer mixture is likely to phase-separate from the resin particles during the polymerization of the monomer mixture, That facilitates achieving the non-spherical shape that is unique to the present invention.

Next, the (meth)acrylic acid ester contained in an aqueous emulsion is polymerized to obtain (meth)acrylic acid ester polymer particles. The polymerization temperature may be suitably selected according to the type of the hydrophobic monomer and the type of the polymerization initiator. The polymerization temperature is preferably from 25 to 110° C. and more preferably from 50 to 100° C. After the polymerization is complete, if necessary, the (meth)acrylic acid ester polymer particles may be filtered out or otherwise separated out from the aqueous medium, residual aqueous medium may be further removed from the (meth)acrylic acid ester polymer particles by, for example, centrifugation, and the resultant (meth)acrylic acid ester polymer particles may be washed in water and a solvent and subsequently dried.

Thus, (meth)acrylic acid ester polymer particles are obtained. The (meth)acrylic acid ester polymer particles are by no means limited in size and shape in any particular manner. The (meth)acrylic acid ester polymer particles used are generally spherical and have particle diameters of 0.1 to 5 μm.

Seed Polymerization Step

In the seed polymerization step, the resin particles obtained in the resin particle preparation step are allowed to absorb a monomer mixture contained in an aqueous emulsion containing a crosslinking monomer in an amount of 5 to 50 wt % as based on the total amount of the monomer mixture, and the absorbed monomer mixture is polymerized.

The monomer mixture contains a vinyl-based polymerizable monofunctional monomer in an amount of 50 to 95 wt % and a crosslinking monomer in an amount of 5 to 50 wt %, both as based on the total amount of the monomer mixture.

The vinyl-based polymerizable monofunctional monomer is a compound with one polymerizable alkenyl group (vinyl group in a broader sense of the term) per molecule. The vinyl-based polymerizable monofunctional monomer preferably differs from the hydrophobic monomer used in the resin particle preparation step, more preferably is more hydrophilic (exhibits a higher water solubility at 20° C.) than the hydrophobic monomer used in the resin particle preparation step, and even more preferably contains at least either one of a vinyl-based polymerizable monomer containing at least one type of hydrophilic substituent selected from the group consisting of a hydroxyl group, a carboxyl group, a sulfo group, and an amino group and a vinyl-based polymerizable monomer having a water solubility of 1 wt % or greater at 20° C. When this is actually the case, the polymer produced from the monomer mixture is likely to phase-separate from the resin particles during the polymerization of the monomer mixture. That facilitates achieving the non-spherical shape that is unique to the present invention. In addition, non-spherical resin particles are manufactured that contain a first, hydrophilic resin component and a second, hydrophobic resin component.

The vinyl-based polymerizable monomer containing at least one type of hydrophilic substituent selected from the group consisting of a hydroxyl group, a carboxyl group, a sulfo group, and an amino group and the vinyl-based polymerizable monomer having a water solubility of 1 wt % or greater at 20° C. may be, for example, those various compounds given as examples under the heading "Hydrophilic resin" and are preferably (meth)acrylic acid esters, of general formula (1), having an alkylene oxide group. When this is actually the case, the polymer produced from the monomer mixture is likely to phase-separate from the resin particles during the polymerization of the monomer mixture. That facilitates achieving the non-spherical shape and non-uniform component distribution that are unique to the present invention.

The (meth)acrylic acid ester, of general formula (1), having an alkylene oxide group is used in an amount of preferably from 0 to 40 wt %, more preferably greater than 0 wt % and less than or equal to 40 wt %, even more preferably from 1 to 40 wt %, still more preferably from 5 to 30 wt %, and most preferably from 10 to 20 wt %, all as based on the total amount of the monomer mixture. If the (meth)acrylic acid ester, of general formula (1), having an alkylene oxide group is used in an amount of less than 1 wt % as based on the total amount of the monomer mixture, the use of the (meth)acrylic acid ester, of general formula (1), having an alkylene oxide group produces practically no effect. On the other hand, if the (meth)acrylic acid ester, of general formula (1), having an alkylene oxide group is used in an amount of greater than 40 wt % as based on the total amount of the monomer mixture, the resultant particles may have decreased polymerization stability with an increased proportion of them sticking together.

The crosslinking monomer is a compound having two or more polymerizable alkenyl groups (vinyl groups in a broader sense of the term) per molecule. The crosslinking monomer is by no means limited in any particular manner and may be any publicly known monomer: specifically, ethylene glycol di(meth)acrylate, trimethylolpropane tri(meth)acrylate, or divinylbenzene, as examples. The crosslinking monomer is used in an amount of preferably from 5 to 50 wt % and more preferably from 10 to 40 wt % as based on the total amount of the monomer mixture. If the crosslinking monomer is used in an amount of less than 5 wt % or greater than 50 wt %, the polymer produced from the monomer mixture is unlikely to phase-separate from the resin particles during the polymerization of the monomer mixture. That makes it difficult to achieve the non-spherical shape and non-uniform component distribution that are unique to the present invention.

The monomer mixture may contain another vinyl-based polymerizable monomer that may or may not be the vinyl-based polymerizable monomer containing at least one type of hydrophilic substituent selected from the group consisting of a hydroxyl group, a carboxyl group, a sulfo group, and an amino group or the vinyl-based polymerizable monomer having a water solubility of 1 wt % or greater at 20° C. The other vinyl-based polymerizable monomer may be, for example, a (meth)acrylic acid derivative, such as n-butyl(meth)acrylate, isobutyl(meth)acrylate, or tert-butyl(meth)acrylate. The other vinyl-based polymerizable monomer is preferably a (meth)acrylic acid ester and more preferably straight-chain alkyl(meth)acrylate. Any one of these compounds may be used alone, or two or more of them may be mixed for use. The other vinyl-based polymerizable monomer is used in an amount of preferably 20 wt % or less and more preferably 10 wt % or less as based on the total amount of the monomer mixture.

In the seed polymerization step, the monomer mixture is dispersed in an aqueous medium to prepare an aqueous emulsion. The aqueous medium may be, for example, one of those media listed under the heading "Resin particle preparation step." The aqueous emulsion may be prepared, for example, by a method using one of the aforementioned fine emulsifiers.

The aqueous emulsion preferably contains a surfactant. The surfactant used here may be, for example, any one of an anionic surfactant, a cationic surfactant, a nonionic surfactant, and an amphoteric surfactant.

The anionic surfactant may be, for example, sodium oleate; a fatty acid soap, such as a castor oil potash soap; an alkyl sulfate salt, such as sodium lauryl sulfate or ammonium lauryl sulfate; an alkylbenzenesulfonate, such as sodium dodecylbenzenesulfonate; an alkylnaphthalenesulfonate; an alkanesulfonate; a dialkylsulfosuccinate salt, such as dioctyl sodium sulfosuccinate; alkenyl succinate (a dipotassium salt); an alkyl phosphate salt; a naphthalenesulfonate formalin condensate; a polyoxyethylene alkyl ether sulfate salt, such as a polyoxyethylene alkyl phenyl ether sulfate salt or sodium polyoxyethylene laurylether sulfate; or a polyoxyethylene alkyl sulfate salt.

The cationic surfactant may be, for example, an alkyl amine salt, such as lauryl amine acetate or stearyl amine acetate; or a quaternary ammonium salt, such as lauryl trimethyl ammonium chloride.

The amphoteric surfactant may be, for example, a lauryl dimethylamine oxide, a phosphate ester-based surfactant, or a phosphite ester-based surfactant. Any one of these surfactants may be used alone, or two or more of them may be used in any combination. Among these surfactants, an anionic surfactant is preferred for dispersion stability in polymerization. Although exact figures may vary depending on the type of the surfactant, these surfactants are used in an amount of preferably 0.1 to 5 parts by weight and more preferably 0.3 to 3 parts by weight as based on 100 parts by weight of the monomer mixture.

The monomer mixture may be mixed with a polymerization initiator if necessary. The polymerization initiator may be mixed with the monomer mixture before being dispersed in the aqueous medium. Alternatively, the polymerization initiator and the monomer mixture may be separately dispersed in aqueous media before being mixed together. The polymerization initiator may be, for example, an organic peroxide, such as benzoyl peroxide, lauroyl peroxide, orthochlorobenzoyl peroxide, orthomethoxybenzoyl peroxide, 3,5,5-trimethylhexanoyl peroxide, tert-butyl peroxy-2-ethylhexanoate, or di-tert-butyl peroxide; or an azo-based compound, such as 2,2'-azobisisobutyronitrile, 1,1'-azobiscyclohexane carbonitrile, or 2,2'-azobis(2,4-dimethyl valeronitrile). The polymerization initiator is used in an amount of preferably 0.1 to 3 parts by weight as based on 100 parts by weight of the monomer mixture.

The droplets of the monomer mixture contained in the resultant aqueous emulsion preferably have smaller particle diameters than the resin particles so that the monomer mixture can be efficiently absorbed by the resin particles.

The resin particles may be added to the aqueous emulsion either directly or after being dispersed in an aqueous medium (e.g., added in the form of an aqueous emulsion). If the resin particles are added after being dispersed in an aqueous medium, an aqueous emulsion containing the resin particles obtained by emulsion polymerization in the resin particle preparation step may be added to an aqueous emulsion containing the monomer mixture. In addition, the resin particles (or the resin particles dispersed in an aqueous medium) may be added to an aqueous medium either at the same time as or before the monomer mixture is dispersed in the aqueous medium. After completing both the addition of the resin particles to the aqueous medium or emulsion and the preparation of the aqueous emulsion, the resin particles are allowed to absorb the monomer mixture contained in the aqueous emulsion. The absorption can be generally carried out by stirring at room temperature (about 20° C.) for 1 to 12 hours the aqueous emulsion to which the resin particles have been added. The absorption may be accelerated by heating the aqueous emulsion to approximately 30 to 50° C.

The resin particles swell as they absorb the monomer mixture. The monomer mixture is absorbed by the resin particles in an amount of preferably from 1 to 125 parts by weight, more preferably from 2 to 60 parts by weight, and even more preferably from 5 to 40 parts by weight, all as based on 1 part by weight of the resin particles. If the monomer mixture is absorbed by the resin particles in an amount of less than 1 part by weight as based on 1 part by weight of the resin particles, the particle diameter does not increase in polymerization as much as it should, which reduces productivity. If the monomer mixture is to be absorbed by the resin particles in an amount of more than 125 parts by weight as based on 1 part by weight of the resin particles, the monomer mixture may not be completely absorbed by the resin particles and suspension-polymerize on its own in the aqueous medium, forming improper particles. The completion of the absorption is determined by observing the growth of the particle diameter under an optical microscope.

In the seed polymerization step, a polymer dispersion stabilizer may be added to the aqueous emulsion to improve the dispersion stability of the obtained non-spherical resin particles. The polymer dispersion stabilizer may be, for example, a polyvinyl alcohol, polycarboxylic acid, a cellulose (e.g., hydroxyethyl cellulose, carboxymethyl cellulose, etc.), or a polyvinylpyrrolidone. In addition, a polymer dispersion stabilizer and an inorganic water-soluble polymer compound, such as sodium tripolyphosphate, may be used together. Among these polymer dispersion stabilizers, a polyvinyl alcohol and a polyvinylpyrrolidone are preferred. The polymer dispersion stabilizer is preferably added in an amount of 1 to 10 parts by weight as based on 100 parts by weight of the monomer mixture.

In addition, in the seed polymerization step, a nitrite, such as sodium nitrite; a sulfite; a hydroquinone; an ascorbate; a water-soluble vitamin B; a citrate, or a water-soluble polymerization inhibitor, such as a polyphenol, may be added to the aqueous emulsion to reduce emulsion particles forming in the aqueous phase. The polymerization inhibitor is preferably added in an amount of 0.02 to 0.2 parts by weight as based on 100 parts by weight of the aqueous medium.

Next, the monomer mixture absorbed by the resin particles is polymerized to obtain non-spherical resin particles. The polymerization temperature may be suitably selected according to the type of the monomer mixture and the type of the polymerization initiator. The polymerization temperature is preferably from 25 to 110° C. and more preferably from 50 to 100° C. The polymerization reaction is preferably carried out at elevated temperature after the monomer mixture is completely absorbed by the resin particles. After the polymerization is complete, if necessary, the non-spherical resin particles may be filtered out or otherwise separated out from the aqueous medium, residual aqueous medium may be further removed from the non-spherical resin particles by, for example, centrifugation, and the resultant non-spherical resin particles may be washed in water and a solvent and subsequently dried.

Method of Manufacturing Non-Spherical Resin Particles Using Resin Solution

Next will be described one of methods of manufacturing non-spherical resin particles in accordance with the present invention: specifically, a method of manufacturing non-spherical resin particles that involves dissolving a resin in a monomer mixture to prepare a solution and polymerizing the solution in an aqueous medium.

This manufacturing method includes: a resin preparation step of polymerizing a hydrophobic monomer containing a (meth)acrylic acid ester having in an ester moiety thereof a $C_2$-$C_{10}$ halogenated alkyl group or alicyclic hydrocarbon group, to prepare a resin having a weight-average molecular weight of from 150,000 to 1,000,000 as measured by gel permeation chromatography; and an aqueous-phase polymerization step of dissolving the resin in a vinyl-based polymerizable monomer to prepare a solution and polymerizing the solution in an aqueous medium.

Resin Preparation Step

The resin preparation step in the manufacturing method using a resin solution may be carried out similarly to the resin particle preparation step in the manufacturing method by seed polymerization mentioned above. The polymerization method used in the resin preparation step is preferably suspension polymerization rather than emulsion polymerization and may be, for example, solution polymerization or bulk polymerization. The following will describe a method of preparing a particulate resin (resin particles) by suspension polymerization, which is however for illustrative purposes only.

In the resin preparation step in which suspension polymerization is used, the hydrophobic monomer described under the heading "Resin particle preparation step" is suspension-polymerized in an aqueous medium to obtain resin particles.

To carry out suspension polymerization, first, an oil phase and an aqueous medium are prepared in separate containers. The oil phase is obtained by mixing and stirring the hydrophobic monomer with another oil phase component used according to need. The other oil phase component used according to need may be, for example, one of the polymerization initiators and molecular weight modifiers listed under the heading "Resin particle preparation step." The polymerization initiator/molecular weight modifier is preferably used in an amount described under the heading "Resin particle preparation step." The mixing and stirring device used in the mixing and stirring is preferably one that provides overall uniformity in the resultant mixture: examples include general-purpose mixers and homogenizers.

The aqueous medium used may be, for example, one of the aqueous media listed under the heading "Resin particle preparation step" above. The aqueous medium is preferably used in an amount of 150 to 1,000 parts by weight as based on 100 parts by weight of the hydrophobic monomer.

A dispersion stabilizer may be added (mixed and stirred) to the aqueous medium to keep the hydrophobic monomer suspended in the aqueous medium for increased stability. The dispersion stabilizer used may be, for example, one of the various polymer dispersion stabilizers (water-soluble polymers) listed under the heading "Seed polymerization step;" or a poorly water-soluble inorganic salt, such as tribasic calcium phosphate, magnesium hydroxide, magnesium pyrophosphate, barium sulfate, calcium carbonate, or silica. The mixing and stirring device used in the mixing and stirring is preferably one that provides overall uniformity in the resultant mixture: examples include general-purpose mixers and homogenizers. Among these dispersion stabilizers, poorly water-soluble inorganic salts having a water solubility of approximately 3 mg or less at normal temperature are preferred because they can be readily removed from resin particles and enable the resin particles to polymerize with a narrower particle size distribution than other dispersion stabilizers. Especially preferred as the dispersion stabilizer is tribasic calcium phosphate, which exhibits a water solubility of 2.5 mg at normal temperature. The dispersion stabilizer is used in an amount of preferably from 0.1 to 20 parts by weight as based on 100 parts by weight of the hydrophobic monomer.

A surfactant may be added (mixed and stirred) to the aqueous medium to keep the hydrophobic monomer suspended in the aqueous medium for increased stability. The surfactant used may be, for example, one of the surfactants listed under the heading "Seed polymerization step." Anionic surfactants are preferred to other surfactants because anionic surfactants enable the resin particles to polymerize with a narrower particle size distribution. The surfactant is preferably blended with the aqueous medium to a concentration of 0.005 to 0.3 wt %. The mixing and stirring device used in the mixing and stirring is preferably one that provides overall uniformity in the resultant mixture: examples include general-purpose mixers and homogenizers.

After the oil phase and the aqueous medium are prepared, the oil phase is added (mixed and stirred) to the aqueous medium to obtain a suspension. Consequently, the oil phase forms oil droplets. Using a homogenizer as the stirring device in the mixing rather than other stirring devices, the size of the oil droplets can be readily adjusted by changing stirring time, revolutions per unit time, and other stirring conditions.

Adjustable oil droplets size will translate into adjustable size of the particles obtained from the oil droplets.

Next, the suspension is heated while being stirred for polymerization of the oil phase to obtain resin particles. The suspension may be heated in a heater, such as an autoclave. If necessary, the obtained resin particles may be filtered, and the residue may be washed in water and subsequently dried to separate the resin particles from the aqueous medium. In addition, the dispersion stabilizer may if necessary be removed before washing the residue in water.

The resin is preferably used in particle form in the succeeding aqueous-phase polymerization step and may be molded into pellets or another shape before being used in the succeeding aqueous-phase polymerization step.

Aqueous-Phase Polymerization Step

Next, in the aqueous-phase polymerization step, the resin obtained in the resin preparation step is dissolved in the monomer mixture described under the heading "Seed polymerization step" to prepare a solution, and the solution is polymerized in an aqueous medium. To dissolve the resin in the monomer mixture, the resin only needs to be mixed with the monomer mixture. Every 1 part by weight of the resin is mixed with preferably 1 to 125 parts by weight of the monomer mixture, more preferably 5 to 50 parts by weight of the monomer mixture, and even more preferably 10 to 30 parts by weight of the monomer mixture. If every 1 part by weight of the resin is mixed with less than 1 part by weight of the monomer mixture, the resin will not sufficiently dissolve. If every 1 part by weight of the resin particles is mixed with more than 125 parts by weight of the monomer mixture, the obtained non-spherical resin particles may contain the second resin component in such a small amount that the non-uniform distribution of the second resin component cannot produce sufficient effect.

The obtained solution may be polymerized in an aqueous medium by, for example, a method similar to the suspension polymerization used in the resin preparation step, using the resin and the monomer mixture in place of the hydrophobic monomer in the suspension polymerization in the resin preparation step. The resin and the monomer mixture may be separately added to the oil phase or first mixed before being added to the oil phase.

Thus, non-spherical resin particles in accordance with the present invention are manufactured that have a circular outline when viewed from a direction in which a maximum projected area is produced and a non-circular outline when viewed from a direction in which a minimum projected area is produced, each of the non-spherical resin particles containing a first resin component derived from a monomer mixture containing a crosslinking monomer and a second resin component derived from a resin (polymer of a hydrophobic monomer), the second resin component residing locally near the surface of the non-spherical resin particles.

The non-spherical resin particles obtained by the manufacturing method in accordance with the present invention have shapes that are controllable through, for example, appropriate adjustment of the composition of ingredients and polymerization conditions. For example, non-spherical resin particles can be manufactured with a semi-spherical shape, a biconvex lens shape, or a mushroom shape or with a horseshoe-like cross-section, purposefully by adjusting the composition and weight-average molecular weight of the resin particles, the amount of the monomer mixture used as based on the resin particles, and the composition of the monomer mixture. For example, if the monomer mixture is used in a large amount as based on the resin particles, the resultant non-spherical resin particles will likely have a horseshoe-like cross-section; if the monomer mixture is used in a small amount as based on the resin particles, the resultant non-spherical resin particles will likely be semi-spherical. If the monomer mixture does not contain a (meth)acrylic acid ester having an alkylene oxide group, the resultant non-spherical resin particles will likely be biconvex lens-shaped; if the monomer mixture contains a small amount of a (meth)acrylic acid ester having an alkylene oxide group, the resultant non-spherical resin particles will likely be semi-spherical; if the monomer mixture contains a large amount of a (meth)acrylic acid ester having an alkylene oxide group, the resultant non-spherical resin particles will likely have a horseshoe-like cross-section. If the resin particles have a low weight-average molecular weight, the resultant non-spherical resin particles will likely have a horseshoe-like cross-section; if the resin particles have an increased weight-average molecular weight, the resultant non-spherical resin particles will likely be semi-spherical; if the resin particles have a further increased weight-average molecular weight, the resultant non-spherical resin particles will likely have a mushroom shape.

Use of Non-Spherical Resin Particles

The non-spherical resin particles in accordance with the present invention are useful as, for example: additives to coating materials (coating compositions) used, for example, as light diffuser coating materials, such as paints, paper coating materials, information recording paper coating materials, and light diffusing films (optical sheets); light diffusion agents that form part of light diffusion resin compositions for the manufacture of light diffusion plates; additives to external preparations, such as cosmetics; and surfactants.

(1) Coating Material

The non-spherical resin particles in accordance with the present invention may be contained as, for example, a coating softener, a coating material flatting agent, or a light diffusion agent in coating materials. The coating material in accordance with the present invention contains the non-spherical resin particles in accordance with the present invention.

The coating material may contain a binder resin where necessary. The binder resin used may be, for example, an organic solvent, a water-soluble resin, or a water-dispersible, emulsion-type aqueous resin and may be any publicly known binder resin. Specific examples of the binder resin include acrylic-based resins (e.g., those with trade names, Dianal® LR-102 and Dianal® BR-106, manufactured by Mitsubishi Rayon Co., Ltd.), alkyd resins, polyester resins, polyurethane resins, chlorinated polyolefin resins, and amorphous polyolefin resins. A suitable binder resin may be selected from these binder resins depending on the adhesion of the paint to the base material to be painted and the environment in which the paint is used.

The non-spherical resin particles are preferably blended in an amount of 0.1 to 1,000 parts by weight as based on 100 parts by weight of the binder although the amount may be suitably adjusted depending on the thickness of the coating to be formed, the average particle diameter of the non-spherical resin particles, the coating method, use, and other conditions related to the coating material containing the binder resin. More specifically, the non-spherical resin particles are blended in an amount of preferably from 5 to 50 mass %, more preferably from 10 to 50 mass %, and even more preferably from 20 to 40 mass %, all as based on the sum of the binder resin (only the solid when an emulsion-type aqueous resin is to be used) and the non-spherical resin particles. If the non-spherical resin particles account for less than 5 mass %, the non-spherical resin particles may not provide sufficient flatting. On the other hand, if the non-spherical resin particles account for more than 50 mass %, the resulting coating material will have excessively high viscosity, and the non-spherical resin particles may disperse insufficiently. That in turn could lead to aesthetic flaws in the coated surface, such as microcracks and roughness in the surface coated with the coating material.

The coating material may contain a medium where necessary. The medium used is preferably a solvent in which the binder resin can be dissolved or a dispersion medium in which the binder resin can be dispersed. The dispersion medium and solvent used may be either an aqueous medium or an oil medium. The oil medium may be, for example, a hydrocarbon-based solvent, such as toluene or xylene; a ketone-based solvent, such as a methyl ethyl ketone or a methyl isobutyl ketone; an ester-based solvent, such as ethyl acetate or butyl acetate; or an ether-based solvent, such as dioxane, ethylene glycol diethylether, or ethylene glycol monobutylether. The aqueous medium may be, for example, water or an alcohol (e.g., isopropanol). Any one of these solvents may be used alone, or two or more of them may be mixed for use. The medium content of the coating material is typically from 20 to 60 wt % as based on the total amount of the coating material.

The coating material may contain other additives, such as a curing agent, a colorant (extender, coloring pigment, metal pigment, mica powder pigment, dye, etc.), a charge inhibitor, a leveling agent, a fluidity regulating agent, an ultraviolet light absorbent, or an optical stabilizer agent.

The base material to be coated with the coating material is by no means limited in any particular manner. Any base material may be used depending on use. For example, for optical uses, glass base materials, transparent base material resins, and like transparent base materials are used as a base material. A light diffuser, such as a light diffusing film, can be manufactured, using a transparent base material as the base material, by applying a coating material (light diffusion coating material) containing no colorant onto the transparent base material to a form a transparent coating. In that case, the non-spherical resin particles act as a light diffusion agent.

The transparent base material resin may be, for example, an acrylic resin; an alkyl(meth)acrylate-styrene copolymer; a polycarbonate; a polyester, such as a polyethylene terephthalate (hereinafter, "PET"); a polyethylene; a polypropylene; or a polystyrene. Preferred among these transparent base material resins when the transparent base material resin is required to exhibit excellent transparency are acrylic resins, alkyl (meth)acrylate-styrene copolymers, polycarbonates, polyesters, and polystyrenes. Any one of these transparent base material resins may be used alone, or two or more of them may be combined for use. The manufactured light diffuser may be used as an illumination cover (e.g., an illumination cover for light-emitting diode (LED) illumination and an illumination cover for fluorescent tube illumination) and a light diffuser (e.g., a light diffusing film and a light diffusion plate).

Flatting paper can be manufactured, using paper as the base material, by applying a coating material (paper coating material) containing no colorant to form a transparent coating.

The coating may be formed of the coating material by any method that is by no means limited in any particular manner. Any publicly known method may be used. The coating may be formed by, for example, spray coating, roll coating, or brush coating. The coating material may, where necessary, be diluted by adding a diluent to it, to adjust its viscosity. The diluent may be, for example, a hydrocarbon-based solvent, such as toluene or xylene; a ketone-based solvent, such as a methyl ethyl ketone or a methyl isobutyl ketone; an ester-based solvent, such as ethyl acetate or butyl acetate; an ether-based solvent, such as dioxane or ethylene glycol diethylether; water; or an alcohol-based solvent. Any one of these diluents may be used alone, or two or more of them may be mixed for use. To manufacture a light diffuser, the coating is preferably formed by such a method that irregularities are formed on the coated surface due to the non-spherical resin particles.

(2) Light Diffusion Resin Composition

The non-spherical resin particles in accordance with the present invention may be dispersed as a light diffusion agent in a transparent base material resin (transparency resin) to use the particles as a light diffusion resin composition. In other words, the light diffusion resin composition obtained may contain the non-spherical resin particles in accordance with the present invention and a transparent base material resin. The light diffusion resin composition may be used as an ingredient for an illumination cover (e.g., an illumination cover for light-emitting diode (LED) illumination and an illumination cover for fluorescent tube illumination) and a light diffuser (e.g., a light diffusion sheet, a light diffusing film, and a light diffusion plate).

The transparent base material resin used is typically a thermoplastic resin that is not a component of the polymer particles that form the non-spherical resin particles. The thermoplastic resin used as the transparent base material resin may be, for example, an acrylic resin, an alkyl(meth)acrylate-styrene copolymer, a polycarbonate, a polyester, a polyethylene, a polypropylene, or a polystyrene. Preferred among these thermoplastic resins when the transparent base material resin is required to exhibit excellent transparency are acrylic resins, alkyl(meth)acrylate-styrene copolymers, polycarbonates, polyesters, and polystyrenes. Any one of these thermoplastic resins may be used alone, or two or more of them may be combined for use.

The non-spherical resin particles are added to the transparent base material resin in an amount of preferably from 0.01 to 40 parts by mass and more preferably from 0.1 to 10 parts by mass as based on 100 parts by mass of the transparent base material resin. If the non-spherical resin particles are added in an amount of less than 0.01 parts by mass, the resultant light diffuser may not exhibit sufficient light diffusion. If the non-spherical resin particles are added in an amount of more than 40 parts by mass, the resultant light diffuser will have sufficient light diffusion, but may exhibit poor optical transparency.

The light diffusion resin composition may be manufactured by any method that is by no means limited in any particular manner, and as an example, manufactured by mixing the non-spherical resin particles and a transparent base material resin by a publicly known, conventional method, for example, mechanical pulverization and mixing. According to the mechanical pulverization and mixing, the light diffusion resin composition may be manufactured by mixing and stirring the non-spherical resin particles and a transparent base material resin using, for example, a Henschel mixer, a V-shaped mixer, a Turbula mixer, a hybridizer, a rocking mixer, or like apparatus.

The light diffusion resin composition may be molded into an illumination cover, a light diffusion sheet, or another light diffuser. When this is the case, for example, a light diffusion agent and a transparent base material resin are mixed in a mixer and kneaded in an extruder or a like melting kneader to form pellets of the light diffusion resin composition. The pellets are then either molded by extrusion or melted and molded by injection, to obtain a light diffuser of any shape.

The light diffusion sheet may be used, for example, as a light diffusion sheet for a liquid crystal display device. The structure of the liquid crystal display device is by no means limited in any particular manner as long as the liquid crystal display device can contain a light diffusion sheet. For example, the liquid crystal display device may include: at least a liquid crystal display panel with a display surface and a backside; a light guide plate disposed on the backside of the liquid crystal display panel; and a light source emitting light incident to a side face of the light guide plate. The liquid crystal display device may further include: a light diffusion sheet on a face of the light guide plate facing the liquid crystal display panel; and a reflection sheet on another face of the light guide plate opposite that face. This light source arrangement is referred to generally as an edge-light backlight arrangement. An alternative light source arrangement to the edge-light backlight arrangement is a direct backlight arrangement in which, specifically, a light source is disposed on the backside of the liquid crystal display panel with at least a light diffusion sheet being located between the liquid crystal display panel and the light source.

External Preparation

The non-spherical resin particles in accordance with the present invention may be used as an ingredient for an external preparation, for example, as a slip enhancement agent for an external preparation. The external preparation in accordance with the present invention contains the non-spherical resin particles in accordance with the present invention. Examples of the external preparation include cosmetics and external medicines.

The cosmetics in the current context are by no means limited in any particular manner as long as they produce an effect if they contain the non-spherical resin particles. Examples of the cosmetics include solid-based cosmetics, such as face powders and makeup foundations; powder-based cosmetics, such as baby powders and body powders; liquid-based cosmetics, such as skin lotions, milky lotions, cosmetic creams, liquid makeup foundations, body lotions, pre-shave lotions, body shampoos, antiperspirants; cleaning cosmetics, such as soaps and scrub cleansers; facial packs; shaving creams; lipsticks; lip balms; cheek colors; eye makeup cosmetics; nail polish cosmetics; hair washing cosmetics; hair coloring preparations; hair dressings; aromatic cosmetics; toothpastes; bath preparations; sunscreen products; and suntan products.

The non-spherical resin particles are blended with these cosmetics in amounts that may vary depending on the types of cosmetics. As an example, for solid-based cosmetics, such as face powders and makeup foundations, the non-spherical resin particles are blended with the cosmetics in an amount of preferably from 1 to 20 wt % and more preferably from 3 to 15 wt %. For powder-based cosmetics, such as baby powders and body powders, the non-spherical resin particles are blended with the cosmetics in an amount of preferably from 1 to 20 wt % and more preferably from 3 to 15 wt %. For liquid-based cosmetics, such as skin lotions, milky lotions, cosmetic creams, liquid makeup foundations, body lotions, and pre-shave lotions, the non-spherical resin particles are blended with the cosmetics in an amount of preferably from 1 to 15 wt % and more preferably from 3 to 10 wt %.

The external medicines in the current context are by no means limited in any particular manner as long as they are applicable to skin. Examples include medical creams, ointments, medical emulsions, and medical lotions. The non-spherical resin particle content of an external medicine may be specified suitably depending on the type of the external medicine, and is preferably from 1 to 80 wt % and more preferably from 5 to 70 wt %. If the non-spherical resin particle content is less than 1 wt % to the total amount of the external medicine, the non-spherical resin particle content may not produce an appreciable effect. On the other hand, if the non-spherical resin particle content is more than 80 wt %, the resultant effect might be less than could be expected for the extra content. This is not desirable in terms of production cost.

These external preparations may be blended with a commonly used base agent or additive suitable for an intended purpose as long as the effect of the present invention is not lost. Examples of the base agent or additive include clay minerals (multifunctional components for gloss enhancement, feel enhancement, etc.; mica, talc, etc.), coloring agents (e.g., red iron oxide, yellow iron oxide, titanium oxide, ultramarine pigments, Prussian blue pigments, carbon black), synthetic dyes (e.g., azo-based dyes), water, lower alcohols (alcohols with 5 or less carbon atoms), higher alcohols (cetyl alcohols and like alcohols with 6 or more carbon atoms), hydrocarbons (e.g., vaseline, liquid paraffins, etc.), silicone oils, vegetable oils, animal oils and fats, waxes, higher fatty acids (e.g., stearic acid and like fatty acids with 12 or more carbon atoms), sterols, fatty acid esters (octyldodecyl myristic acid esters, oleic acid esters, etc.), metal soaps, moisturizing agents, anti-inflammatory agents, skin-lightening agents, anti-UV skin care agents, disinfectants, antiperspirants, algefacients, perfumes, surfactants (polyethylene glycol, etc.), polymer compounds, antiseptics/disinfectants, antioxidants, ultraviolet light absorbents, acrylic resin particles (poly(meth)acrylic acid ester particles), silicone-based particles, resin particles (e.g., polystyrene particles), non-spherical resin particles other than those in accordance with the present invention, pH adjusters (e.g., triethanol amine), specially blended additives, and medical active ingredients.

(4) Surfactant

If the surface of the non-spherical resin particles in accordance with the present invention is partially formed of the first, hydrophilic resin component with the rest of the surface being formed of the second, hydrophobic resin component, the non-spherical resin particles have a function as a surfactant because the non-spherical resin particles have both a hydrophilic part and a hydrophobic part on the surface. Therefore, the non-spherical resin particles in accordance with the present invention are expected to be used as an emulsifier, a detergent, a charge inhibitor, a lubrication agent, a fabric softener, an antifog/spreading agent, and a dye mordant, all for dispersing and emulsifying either oil or a like oil medium (or oil phase component) in an aqueous medium (or aqueous phase component) or an aqueous medium (or aqueous phase component) in an oil medium (or oil phase component).

(5) Emulsion

The emulsion in accordance with the present invention contains the non-spherical resin particles in accordance with the present invention. In the emulsion in accordance with the present invention, the non-spherical resin particles in accordance with the present invention function as an emulsifier. The emulsion in accordance with the present invention contains both an aqueous phase component and an oil phase component and may be either of an oil-droplet-in-water type in which droplets of an oily component are dispersed in an aqueous component or of a water-droplet-in-oil type in which droplets of an aqueous component are dispersed in an oily component.

The oily component may be, for example, a higher alcohol (cetyl alcohol or a like alcohol with 6 or more carbon atoms), a hydrocarbon (e.g. vaseline, a liquid paraffin, etc.), a silicone oil, a vegetable oil, an animal oil and fat, a wax, a higher fatty acid (e.g., stearic acid or a like fatty acid with 12 or more carbon atoms), a sterol, a perfume, or an antiseptic. The aqueous component may be, for example, water, a pH adjuster (e.g., triethanol amine), or a clay mineral.

The emulsion in accordance with the present invention may be used, for example, as an emulsion-type makeup foundation that is one of the external preparations listed above.

Optical Member

The optical member in accordance with the present invention contains a base material and non-spherical resin particles in accordance with the present invention. Each non-spherical resin particle is semi-spherical and made of a semi-spherical surface portion and a plane portion. The non-spherical resin particles are arranged on the base material so that their plane portions face the base material.

The base material used may be, for example, a transparent film base material, such as a film of one of the various resins listed as examples of the transparent base material resin under the heading "(1) Coating material"; a light-transmitting base material, other than the transparent film base material, such as a transparent resin plate or glass plate made of one of the various resins; or a light-reflecting base material, such as a metal film or a metal plate. When a light-transmitting base material, such as a transparent film base material is used as the base material, the optical member in accordance with the present invention functions as a light transmitter that exhibits both light diffusion and light converging properties and may hence be used as, for example, a light diffuser or a light converging member. When a transparent film base material is used as the base material, the optical member in accordance with the present invention functions as a light-transmitting film that exhibits both light diffusion and light converging properties and may hence be used as, for example, a light diffusing film or a light converging film. When a light-reflecting base material is used as the base material, the optical member in accordance with the present invention functions as a light reflector that exhibits both light diffusion and light converging properties and may hence be used as, for example, an light diffuser/reflector or a light converging member.

The optical member in accordance with the present invention may be manufactured by spreading, on the surface of an aqueous liquid medium (e.g., water) in a container (e.g., beaker) containing the aqueous liquid medium, a dispersion liquid (coating material) obtained by dispersing non-spherical (semi-spherical) resin particles in an aqueous dispersion medium, subsequently placing a base material on the surface to transfer the spread dispersion liquid onto the base material, and drying the base material. The aqueous dispersion medium used may be, for example, an alcohol, such as isopropanol. The dispersion liquid may be spread gently, for example, using a dropper.

EXAMPLES

The following will describe the present invention by way of examples and comparative examples, which by no means limits the present invention.

Measurement of Weight-Average Molecular Weight

Weight-average molecular weights (weight-average polystyrene (PS)-equivalent molecular weights) were measured by gel permeation chromatography (GPC) as detailed below. First, a sample (50 mg) was dissolved in 10 ml of tetrahydrofuran (THF). The obtained solution was filtered with a chromatodisc (non-aqueous, 0.45 μm). The obtained filtrate was analyzed by GPC to measure its weight-average PS-equivalent molecular weight under the following conditions.

GPC Apparatus: "Gel Permeation Chromatograph HLC-8020" manufactured by Tosoh Corporation Column: Two sets of "TSK gel GMH XL-L" manufactured by Tosoh Corporation (7.8 mm in diameter×30 cm in length)

Column Temperature: 40° C.

Carrier Gas: Tetrahydrofuran (THF)

Flow Rate of Carrier Gas: 1 mL/minute

Injection and Pumping Temperature: 35° C.

Detector: RI (Differential Refractive Index Detector)

Injection: 100 μL

Standard Polystyrene for Drawing Calibration Curve from which Weight-average PS-equivalent Molecular Weight is to be Calculated: "Shodex" manufactured by Showa Denko K.K. (weight-average molecular weight=1,030,000) and a standard polystyrene for drawing calibration curve manufactured by Tosoh Corporation (weight-average molecular weight=5,480,000, 3,840,000, 355,000, 102,000, 37,900, 9,100, 2,630, and 870)

Method of Measuring Average Particle Diameter of Seed Particles

The average particle diameter of seed particles was measured by a laser diffraction particle size analyzer ("LS230" manufactured by Beckman Coulter, Inc.). Specifically, seed particles (0.1 grams) and a 0.1 wt % non-ionic surfactant solution (10 ml) were introduced into a test tube and mixed for 2 seconds in a touch mixer ("Touch Mixer MT-31" manufactured by Yamato Scientific Co., Ltd.). Thereafter, the seed particles in the test tube were dispersed over 10 minutes using a commercially available ultrasonic cleaner ("Ultrasonic Cleaner VS-150" manufactured by Velvo-clear Co., Ltd.) to obtain a dispersion liquid. With the dispersion liquid being placed under ultrasonic radiation, the average particle diameter of the seed particles in the dispersion liquid was measured by a laser diffraction particle size analyzer ("LS230" manufactured by Beckman Coulter, Inc.). The optical model used for the measurement was adjusted to the refractive index of the seed particles prepared. When a single monomer was used to prepare the seed particles, the refractive index of the homopolymer of that monomer was used as the refractive index of the seed particles. When two or more monomers were used to prepare the seed particles, the weighted average of the refractive indices of the homopolymers of those monomers, using the amount of each monomer as its weight, was used as the refractive index of the seed particles.

Method of Measuring Lengths A to I of Non-Spherical Resin Particles

Each length A to I of the non-spherical resin particles was measured by, first, observing 30 given non-spherical resin particles under a scanning electron microscope (×5,000 to ×10,000), "JSM-6360LV" (manufactured by JEOL Ltd.), to measure the length of the part of the non-spherical resin particles corresponding to that length A to I. The 30 measurements were then averaged to obtain length A to I.

Method of Measuring Sphere-Equivalent Volume-Average Particle Diameter of Non-Spherical Resin Particles The sphere-equivalent volume-average particle diameter of non-spherical resin particles was calculated by filling fine pores (pore diameter=50 to 280 μm) with an electrolyte solution and determining a volume from the changes of the conductivity of the electrolyte solution during the passage of the particles through the electrolyte solution. Specifically, the sphere-equivalent volume-average particle diameter of the non-spherical resin particles was the volume-average particle diameter (arithmetic average of diameters obtained from volume-based particle size distribution) measured by the Coulter Principle using a Coulter counter analyzer Multisizer II (manufactured by Beckman Coulter, Inc.). Before the measurement, the Multisizer II was calibrated using an aperture suitable for the diameters of the particles to be measured according to the "Reference MANUAL FOR THE COULTER MULTISIZER (1987)" published by Coulter Electronics Limited.

Specifically, non-spherical resin particles (0.1 grams) and a 0.1 wt % aqueous solution (10 ml) of a nonionic surfactant were introduced into a commercially available glass test tube and mixed for 2 seconds in a touch mixer ("ouch Mixer MT-31" manufactured by Yamato Scientific Co., Ltd.). Thereafter, the non-spherical resin particles in the test tube were preliminarily dispersed for 10 seconds using a commercially available ultrasonic cleaner ("Ultrasonic Cleaner VS-150" manufactured by Velvo-clear Co., Ltd.) to obtain a dispersion liquid. Next, while gently stirring, the dispersion liquid was dispensed dropwise using a dropper into a beaker filled with a measurement electrolyte solution ("ISOTON® II" manufactured by Beckman Coulter, Inc.) that came with the Multisizer II. The density meter on the screen of the main body of the Multisizer II was adjusted to yield readings of about 10%. Next, an aperture size (diameter), a current (aperture current), a gain, and a polarity (of the inner electrode) were entered on the main body of the Multisizer II according to the "REFERENCE MANUAL FOR THE COULTER MULTISIZER (1987)" published by Coulter Electronics Limited, and the volume-based particle size distribution was measured manually. The content of the beaker was stirred so gently during measurement that no bubbles could form. The measurement was terminated when the volume-based particle size distribution of 100,000 non-spherical resin particles was measured.

Exemplary Emulsion Synthesis 1 as Preparation of Seed Particles

A separable flask equipped with a stirrer, a thermometer, and a reflux condenser was charged with 600 grams of water as an aqueous medium, 100 grams of methyl methacrylate as a (meth)acrylic acid ester, and 0.5 grams of n-dodecyl mercaptan as a chain transfer agent. The space in the separable flask was replaced with nitrogen while stirring the content of the separable flask with a stirrer, and the internal temperature of the separable flask was elevated to 70° C. Then, 0.5 grams of potassium persulfate as a polymerization initiator was added to the content of the separable flask while keeping the internal temperature of the separable flask at 70° C. The content of the separable flask was subjected to polymerization reaction for 8 hours while keeping the internal temperature of the separable flask at 70° C., to obtain an emulsion (aqueous emulsion). The obtained emulsion contained 14 wt % solid (methyl methacrylate polymer) spherical particles with an average particle diameter of 0.4 µm and a weight-average molecular weight of 600,000.

Exemplary Emulsion Synthesis 2 as Preparation of Seed Particles

The same procedures were followed as in exemplary emulsion synthesis 1 as preparation of seed particles, except that no n-dodecyl mercaptan was used, to obtain an emulsion through polymerization. The obtained emulsion contained 14 wt % solid (methyl methacrylate polymer) spherical fine particles with an average particle diameter of 0.43 µm and a weight-average molecular weight of 850,000.

Exemplary Seed Particle Preparation 1

A separable flask equipped with a stirrer, a thermometer, and a reflux condenser was charged with 550 grams of water as an aqueous medium, 70 grams of the emulsion obtained in exemplary synthesis 1, 100 grams of 2,2,2-trifluoroethyl methacrylate as a (meth)acrylic acid ester containing a $C_2$-$C_{10}$ halogenated alkyl group in an ester moiety thereof, and 0.3 grams of n-dodecyl mercaptan as a chain transfer agent. The space in the separable flask was replaced with nitrogen while stirring the content of the separable flask with a stirrer, and the internal temperature of the separable flask was elevated to 70° C. Then, 0.5 grams of potassium persulfate as a polymerization initiator was added while keeping the internal temperature of the separable flask at 70° C. Thereafter, the content of the separable flask was subjected to polymerization reaction for 8 hours while keeping the internal temperature of the separable flask at 70° C. Thus, an emulsion containing seed particles (hereinafter, "seed particle-containing emulsion") was obtained.

The obtained seed particle-containing emulsion contained 14 wt % solid spherical particles (seed particles) with an average particle diameter of 1.0 µm and a weight-average molecular weight of 620,000.

Exemplary Seed Particle Preparation 2

The same procedures were followed as in exemplary emulsion synthesis 1, except that the emulsion (70 grams) obtained in exemplary synthesis 2 was used in place of the emulsion (70 grams) obtained in exemplary synthesis 1 and also that no n-dodecyl mercaptan was used, to obtain a seed particle-containing emulsion through polymerization.

The obtained seed particle-containing emulsion contained 14 wt % solid spherical fine particles with an average particle diameter of 1.1 µm and a weight-average molecular weight of 820,000.

Exemplary Seed Particle Preparation 3

The same procedures were followed as in exemplary emulsion synthesis 1, except that methyl methacrylate (100 grams) was used in place of 2,2,2-trifluoroethyl methacrylate (100 grams) and also that no n-dodecyl mercaptan was used, to obtain a seed particle-containing emulsion through polymerization.

The obtained seed particle-containing emulsion contained 14 wt % spherical fine particles with an average particle diameter of 1.0 µm and a weight-average molecular weight of 25,000.

Exemplary Seed Particle Preparation 4

The same procedures were followed as in exemplary emulsion synthesis 1, except that cyclohexyl methacrylate (100 grams) was used in place of 2,2,2-trifluoroethyl methacrylate (100 grams), to obtain a seed particle-containing emulsion through polymerization.

The obtained seed particle-containing emulsion contained 14 wt % spherical fine particles with an average particle diameter of 0.95 µm and a weight-average molecular weight of 590,000.

Exemplary 2,2,2-Trifluoroethyl Methacrylate-Methyl Methacrylate Copolymer Preparation 1

First, benzoyl peroxide (0.5 parts by weight) as a polymerization initiator and n-dodecyl mercaptan (3 parts by weight) as a chain transfer agent were dissolved in a vinyl-based polymerizable monomer (hydrophobic monomer), composed of 85 parts by weight of 2,2,2-trifluoroethyl methacrylate and 15 parts by weight of methyl methacrylate, as a (meth)acrylic acid ester containing a $C_2$-$C_{10}$ halogenated alkyl group in an ester moiety thereof, to prepare a mixed solution.

Next, deionized water (500 parts by weight) as an aqueous medium in which sodium lauryl sulfate (0.05 parts by weight) as an anionic surfactant had been dissolved was put into a polymerization vessel equipped with a stirrer and a thermometer. In this deionized water, tribasic calcium phosphate (50 parts by weight) as a poorly water-soluble inorganic salt was dispersed to obtain a dispersion liquid. The mixed solution prepared in advance was added to this dispersion liquid. The obtained dispersion liquid was stirred for 10 minutes with a high-speed emulsification and dispersion device ("T.K homomixer" manufactured by PRIMIX Corporation) at a stirring rate of 3,000 rpm so that the mixed solution could produce droplets with diameters of about 20 μm. Next, the polymerization vessel was heated to 80° C. to carry out suspension polymerization while stirring. The polymerization vessel was subsequently cooled down. The obtained suspension was filtered, washed, and then dried, to obtain a methyl methacrylate-2,2,2-trifluoroethyl methacrylate copolymer in particle form. The obtained particles had a weight-average molecular weight of 350,000.

Example 1

A 5-L reaction vessel equipped with a stirrer and a thermometer was charged with methyl methacrylate (600 grams), ethylene glycol dimethacrylate (300 grams) (crosslinking monomer; 30 wt % as based on the total amount of the vinyl-based polymerizable monomer), and poly(ethylene glycol-propylene glycol)monomethacrylate (100 grams) ("Blemmer® 50 PEP-300" manufactured by NOF Corporation, a mixture of compounds of general formula (1) where $R_1$ was $CH_3$, $R_2$ was $C_2H_5$, $R_3$ was $C_3H_6$, $R_4$ was H, m was 3.5 on average, and n was 2.5 on average) as a monomer mixture and 2,2'-azobisisobutyronitrile (6 grams) as a polymerization initiator. The whole content was mixed by stirring with a stirrer. The obtained mixture was mixed with ion exchanged water (1 L) containing sodium dioctylsulfosuccinate (10 grams) as an anionic surfactant. The whole content was stirred over 10 minutes with a high-speed emulsification and dispersion device ("T.K homomixer" manufactured by PRIMIX Corporation) as a fine emulsifier at a stirring rate of 8,000 rpm, to obtain an aqueous emulsion. To this aqueous emulsion, the seed particle-containing emulsion (360 grams) prepared in exemplary seed particle preparation 1, having an average particle diameter of 1.0 μm, was added while stirring with a stirrer.

After continuous 3-hour stirring with a stirrer, the aqueous emulsion was observed under an optical microscope, and it was found that the vinyl-based polymerizable monomer in the aqueous emulsion was absorbed by the seed particles (swell ratio=about 20 times). Thereafter, an aqueous solution (2000 grams) in which a polyvinyl alcohol ("PVA-224E" manufactured by Kuraray Co., Ltd.) (40 grams) as a polymer dispersion stabilizer had been dissolved was put in a reaction vessel and polymerized at 60° C. over 6 hours while stirring with a stirrer. The post-polymerization reaction solution was filtered to separate out resin particles from the reaction solution. The separated resin particles were well washed in warm water and subsequently dried, to obtain resin particles.

Figure 5:
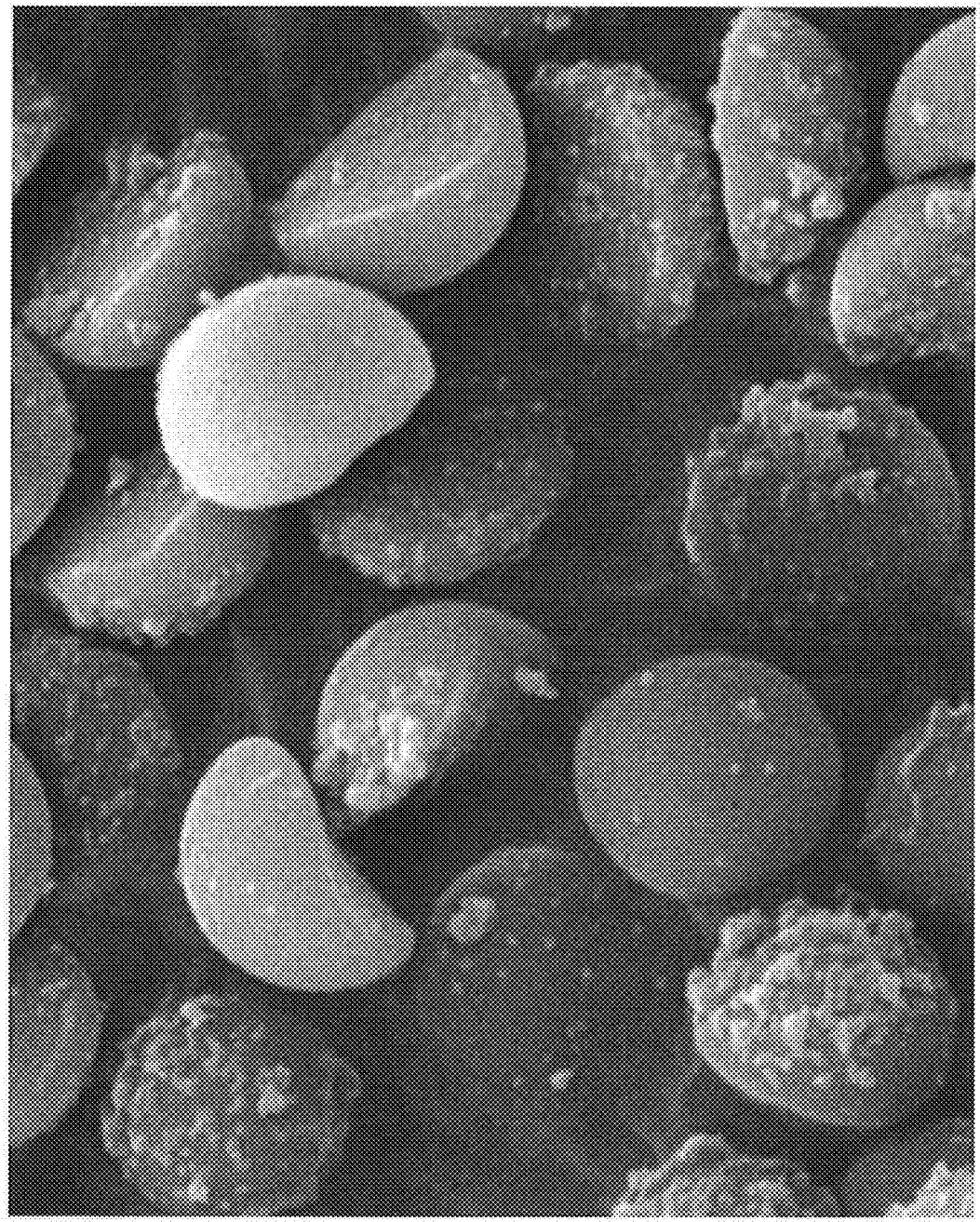
FIG. 5 is an SEM (scanning electron microscope) image generated by SEM-imaging the surface of non-spherical resin particles obtained in example 1 of the present invention.

The obtained resin particles were imaged under a scanning electron microscope (SEM), to obtain the SEM image in FIG. 5. The obtained resin particles were non-spherical (semi-spherical) as illustrated in FIG. 5. The particle diameter A and minor axis F of the obtained non-spherical (semi-spherical) resin particles were measured according to the aforementioned measuring method (A=2.85 μm, F=1.70 μm, and F/A=0.596). The sphere-equivalent volume-average particle diameter of the non-spherical resin particles measured according to the aforementioned measuring method was 2.70 μm.

Figure 6:
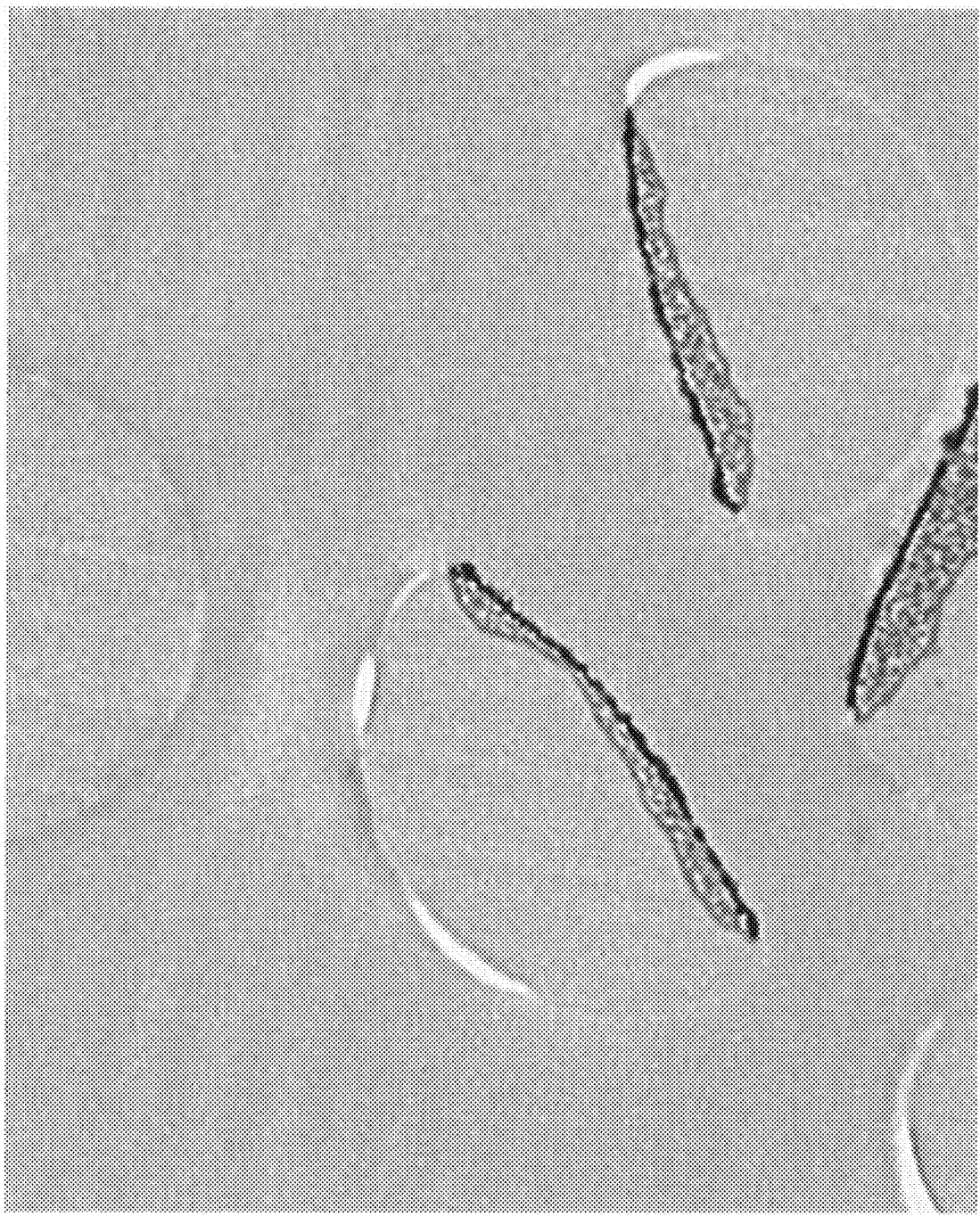
FIG. 6 is a TEM (transmission electron microscope) image generated by TEM-imaging the cross-section of non-spherical resin particles obtained in example 1 of the present invention.

The obtained non-spherical (semi-spherical) resin particles were embedded in an embedding resin (epoxy resin). Subsequently, some non-spherical resin particles embedded in the embedding resin were cut to obtain thin pieces of them including their centers. The thin pieces were stained with a stain (ruthenium tetroxide) and imaged under a transmission electron microscope (TEM) to obtain the TEM image in FIG. 6. The obtained non-spherical (semi-spherical) resin particles, as illustrated in FIG. 6, had a first resin component (thin colored, larger gray portion) derived from the monomer mixture containing the crosslinking monomer and a second resin component (thick colored, smaller gray portion) derived from seed particles, with the second resin component residing locally near the surface of the non-spherical resin particles. Besides, the obtained non-spherical (semi-spherical) resin particles, as illustrated in FIG. 6, had the substantially entire surface of their plane portion formed of the second resin component and the rest of their surface formed of the first resin component. Note that in the TEM image in FIG. 6 and those in FIGS. 8, 10, 16, and 18 related to examples of the latter sub-step, the black portions present in the second resin component surface are caused by the stain that had entered the interface between the non-spherical resin particle and the embedding resin and are no indication of presence of a component other than the first and second resin components in the non-spherical resin particle.

Example 2

The same procedures were followed as in example 1, except that the seed particle-containing emulsion prepared in exemplary seed particle preparation 1 was used in an amount of 180 grams instead of 360 grams, to obtain resin particles.

Figure 7:
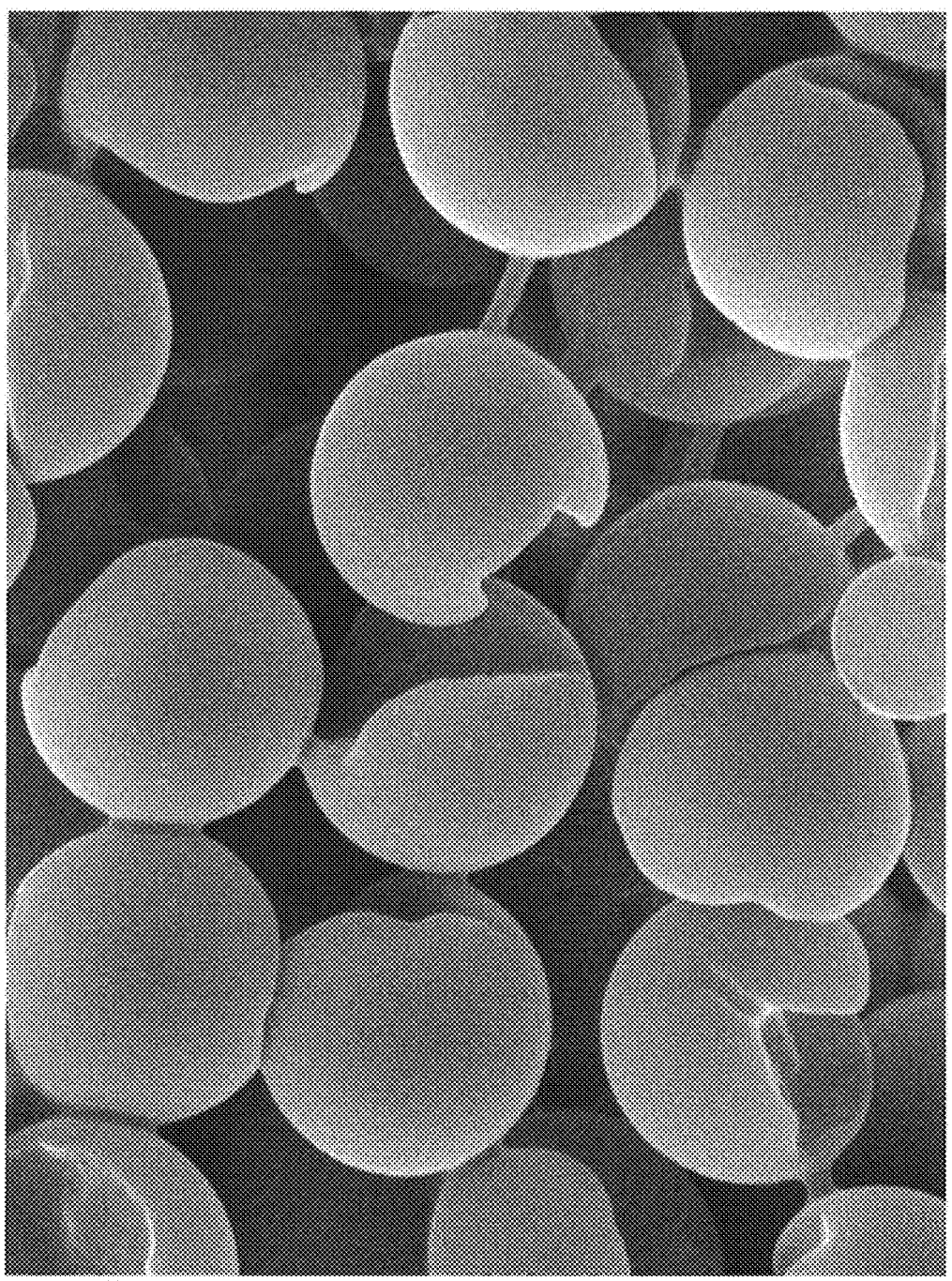
FIG. 7 is an SEM image generated by SEM-imaging the surface of non-spherical resin particles obtained in example 2 of the present invention.

The obtained resin particles were imaged under an SEM, to obtain the SEM image in FIG. 7. The obtained resin particles were non-spherical and had a horseshoe-like cross-section as illustrated in FIG. 7. The particle diameter A, notch section depth B, and notch section opening width C of the obtained non-spherical resin particles with a horseshoe-like cross-section were measured according to the aforementioned measuring method (A=3.45 μm, B=1.17 μm, C=1.69 μm, B/A=0.339, and C/A=0.490). The sphere-equivalent volume-average particle diameter of the non-spherical resin particles measured according to the aforementioned measuring method was 3.50 μm.

Figure 8:
FIG. 8 is a TEM image generated by TEM-imaging the cross-section of a non-spherical resin particle obtained in example 2 of the present invention.

The obtained non-spherical resin particles with a horseshoe-like cross-section were embedded in an embedding resin (epoxy resin). Subsequently, some non-spherical resin particles embedded in the embedding resin were cut to obtain thin pieces of them including their centers. The thin pieces were stained with a stain (ruthenium tetroxide) and imaged under a TEM to obtain the TEM image in FIG. 8. The obtained non-spherical resin particles with a horseshoe-like cross-section, as illustrated in FIG. 8, had a first resin component (thin colored, larger gray portion) derived from the monomer mixture containing the crosslinking monomer and a second resin component (thick colored, smaller gray portion) derived from seed particles, with the second resin component residing locally near the surface of the non-spherical resin particles. Besides, the obtained non-spherical resin particles with a horseshoe-like cross-section, as illustrated in FIG. 8, had more than half of their notch section surface formed of the second resin component and the rest of their surface formed of the first resin component.

Example 3

The same procedures were followed as in example 1, except that methyl methacrylate (700 grams) was used in place of methyl methacrylate (600 grams) and poly(ethylene glycol-propylene glycol)monomethacrylate (100 grams), to obtain resin particles.

Figure 9:
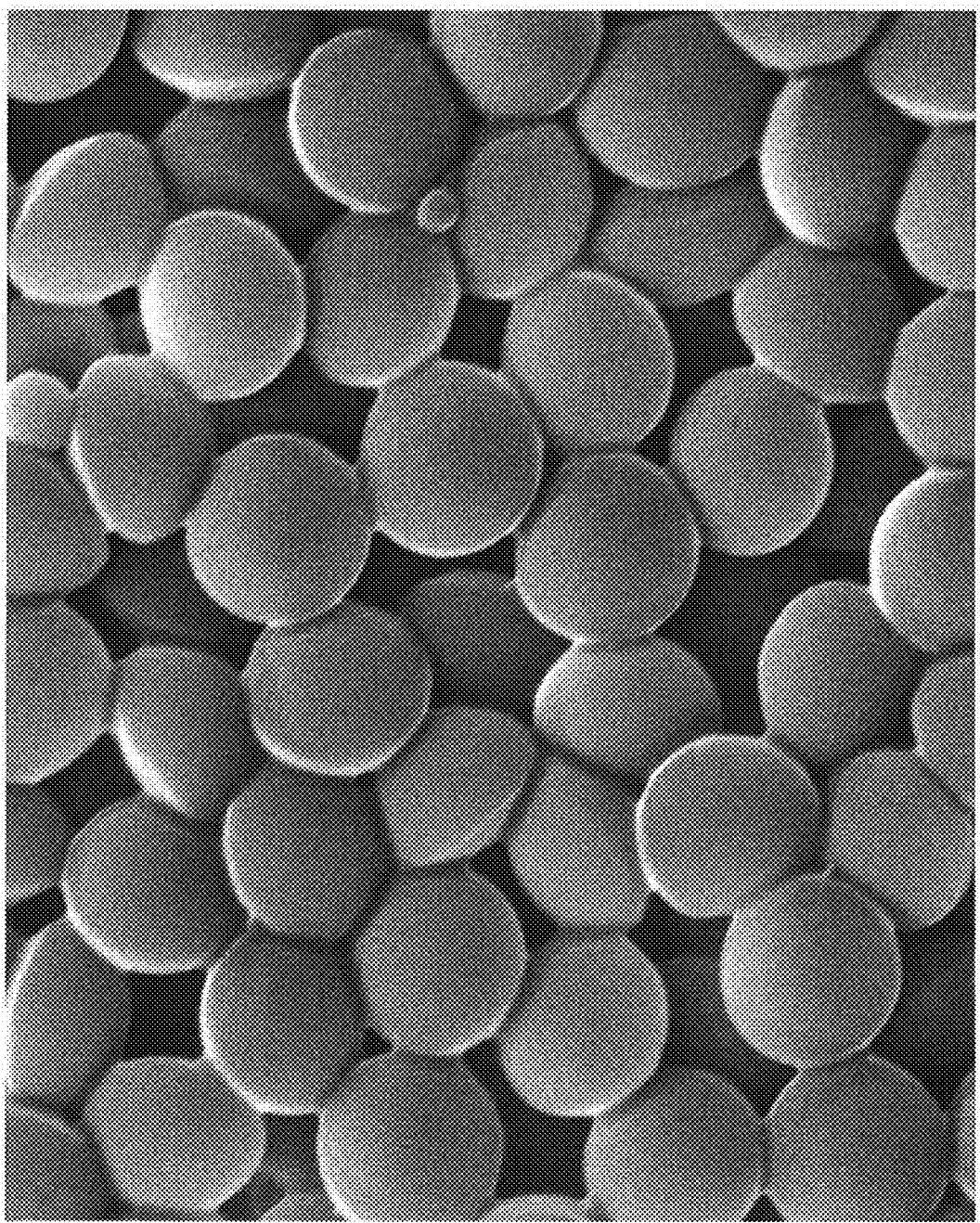
FIG. 9 is an SEM image generated by SEM-imaging the surface of non-spherical resin particles obtained in example 3 of the present invention.

The obtained resin particles were imaged under an SEM, to obtain the SEM image in FIG. 9. The obtained resin particles were non-spherical (biconvex lens-shaped) as illustrated in FIG. 9. The particle diameter A of the obtained non-spherical (biconvex lens-shaped) resin particles, the height H of the larger planoconvex lens-shaped section, and the height I of the smaller planoconvex lens-shaped section were measured according to the aforementioned measuring method (A=2.7 µm, H=1.23 µm, I=0.58 µm, H/A=0.456, and I/A=0.215). The sphere-equivalent volume-average particle diameter of the non-spherical resin particles measured according to the aforementioned measuring method was 2.58 µm.

Figure 10:
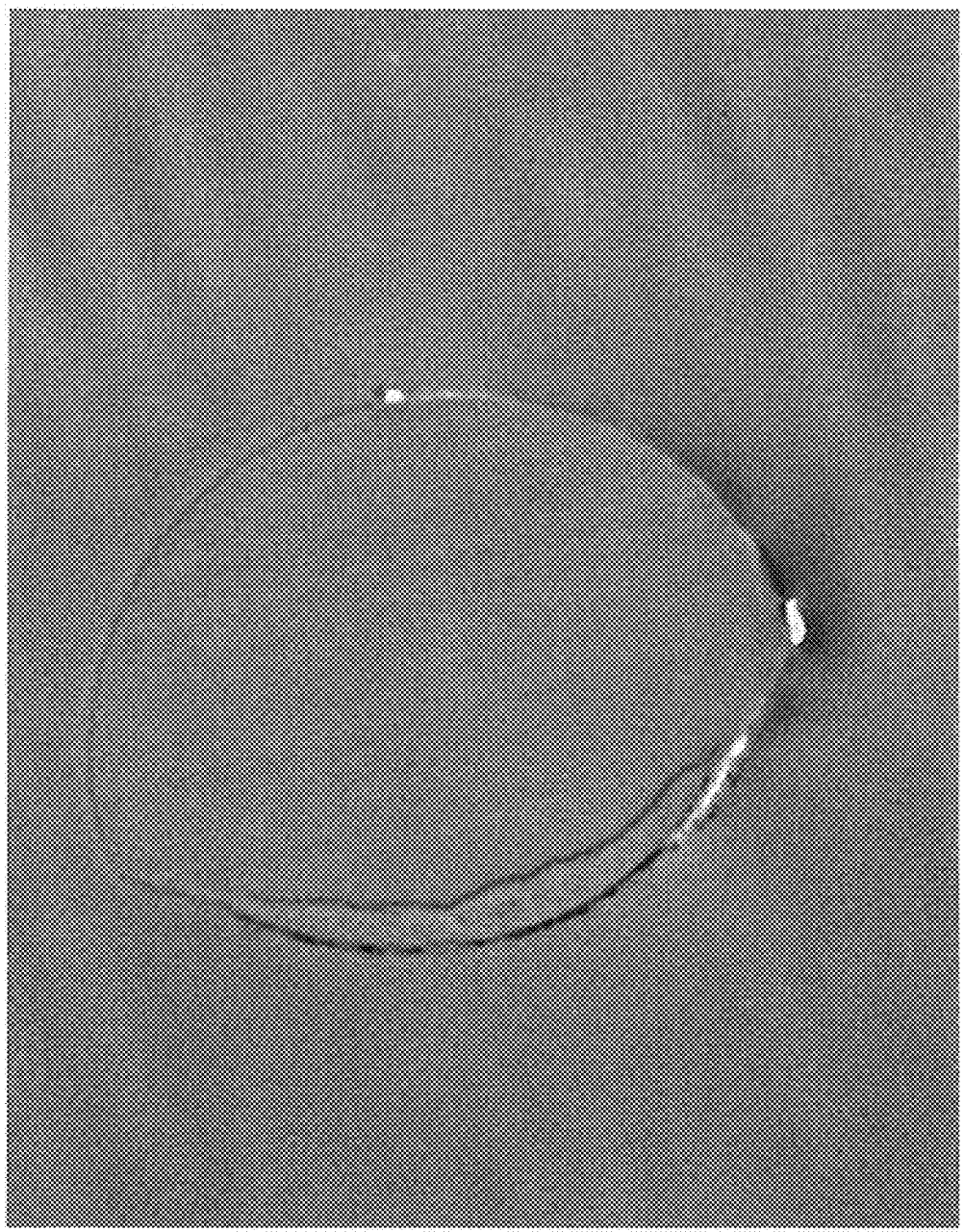
FIG. 10 is a TEM image generated by TEM-imaging the cross-section of a non-spherical resin particle obtained in example 3 of the present invention.

The obtained non-spherical (biconvex lens-shaped) resin particles were embedded in an embedding resin (epoxy resin). Subsequently, some non-spherical resin particles embedded in the embedding resin were cut to obtain thin pieces of them including their centers. The thin pieces were stained with a stain (ruthenium tetroxide) and imaged under a TEM to obtain the TEM image in FIG. 10. The obtained non-spherical (biconvex lens-shaped) resin particles, as illustrated in FIG. 10, had a first resin component (thick colored, larger gray portion) derived from the monomer mixture containing the crosslinking monomer and a second resin component (thin colored, smaller gray portion) derived from seed particles, with the second resin component residing locally near the surface of the non-spherical resin particles. Besides, the obtained non-spherical (biconvex lens-shaped) resin particles, as illustrated in FIG. 10, had the substantially entire surface of their smaller planoconvex lens-shaped section formed of the second resin component and the rest of their surface formed of the first resin component.

Example 4

The same procedures were followed as in example 3, except that the seed particle-containing emulsion (360 grams) prepared in exemplary seed particle preparation 2 was used in place of the seed particle-containing emulsion (360 grams) prepared in exemplary seed particle preparation 1, to obtain resin particles.

Figure 11:
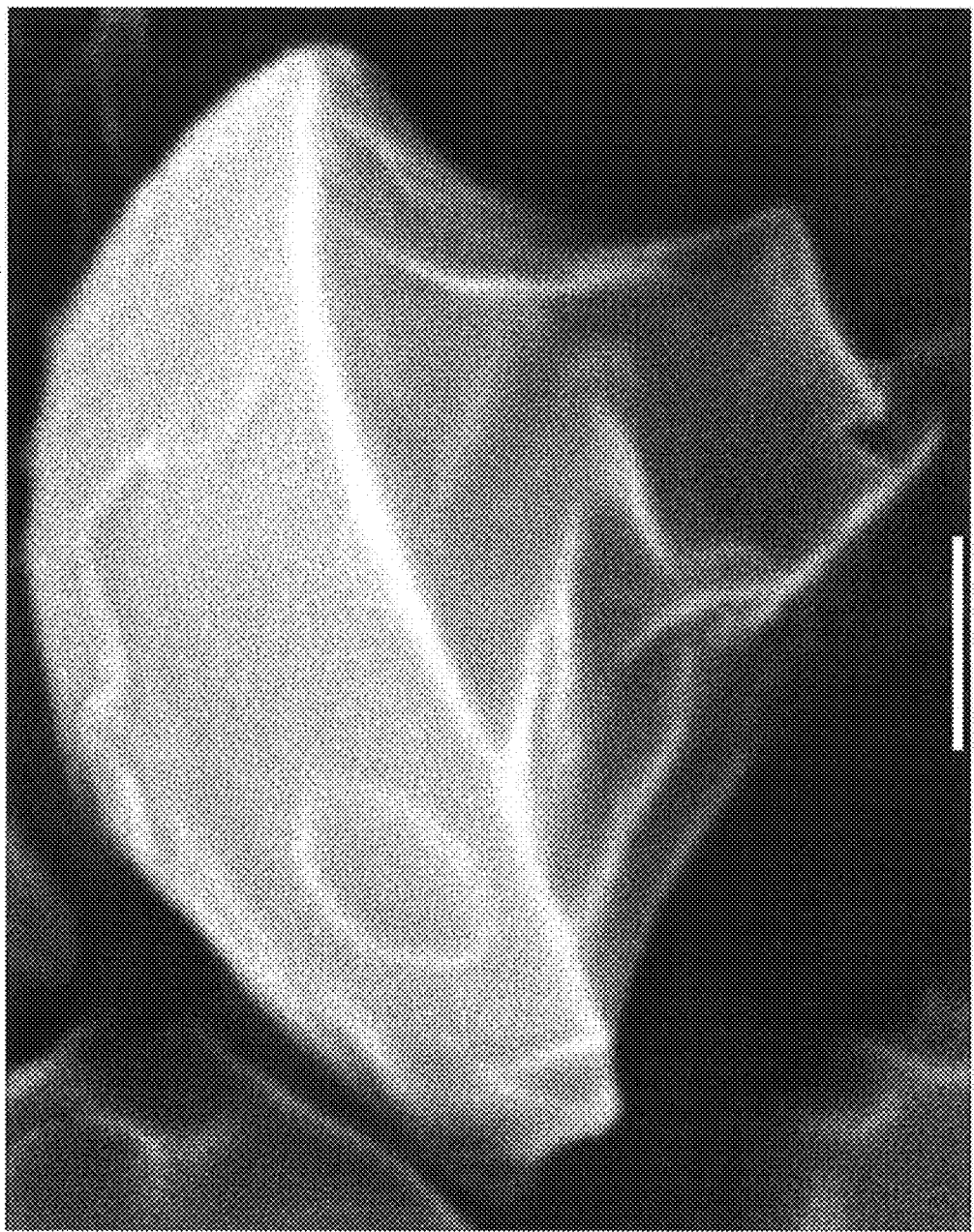
FIG. 11 is an SEM image generated by SEM-imaging the surface of a non-spherical resin particle obtained in example 4 of the present invention.

The obtained resin particles were imaged under an SEM, to obtain the SEM image in FIG. 11. The obtained resin particles were non-spherical and had a mushroom shape as illustrated in FIG. 11. The particle diameter A of the obtained non-spherical resin particles with a mushroom shape, the width D1 at the end of the stem section, the width D2 at the mid-portion of the stem section, and the height E of the stem section were measured according to the aforementioned measuring method (A=2.78 µm, D1=0.7 µm, D2=1.61 µm, E=1.49 µm, D1/A=0.252, D2/A=0.579, and E/A=0.536). The sphere-equivalent volume-average particle diameter of the non-spherical resin particles measured according to the aforementioned measuring method was 2.60 µm.

Figure 12:
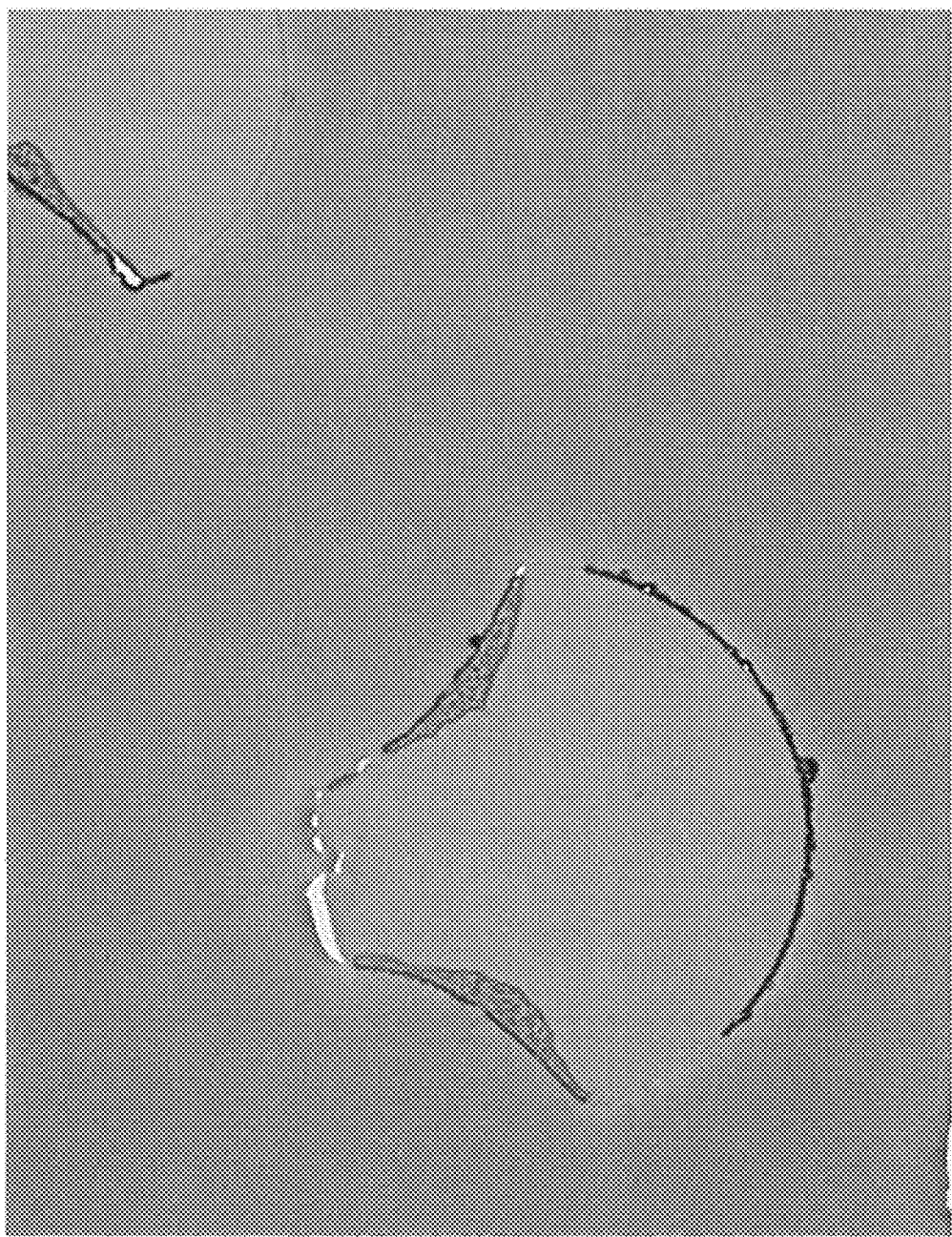
FIG. 12 is a TEM image generated by TEM-imaging the cross-section of a non-spherical resin particle obtained in example 4 of the present invention.

The obtained non-spherical resin particles with a mushroom shape were embedded in an embedding resin (epoxy resin). Subsequently, some non-spherical resin particles embedded in the embedding resin were cut to obtain thin pieces of them including their centers. The thin pieces were stained with a stain (ruthenium tetroxide) and imaged under a TEM to obtain the TEM image in FIG. 12. The obtained non-spherical resin particles with a mushroom shape, as illustrated in FIG. 12, had a first resin component (thin colored, larger gray portion) derived from the monomer mixture containing the crosslinking monomer and a second resin component (thick colored, smaller gray portion) derived from seed particles, with the second resin component residing locally near the surface of the non-spherical resin particles. Besides, the obtained non-spherical resin particles with a mushroom shape, as illustrated in FIG. 12, had more than half of their stem section surface formed of the second resin component and the rest of their surface formed of the first resin component. Note that in the TEM image in FIG. 12, the black portions present in the first and second resin component surfaces are caused by the stain that had entered the interface between the non-spherical resin particle and the embedding resin and are no indication of presence of a component other than the first and second resin components in the non-spherical resin particle.

Example 5

First, the 2,2,2-trifluoroethyl methacrylate-methyl methacrylate copolymer (resin particles) (5 parts by weight) prepared in exemplary 2,2,2-trifluoroethyl methacrylate-methyl methacrylate copolymer preparation 1 and benzoyl peroxide (0.5 parts by weight) and azobisisobutyronitrile (0.5 parts by weight) as polymerization initiators were dissolved in a monomer mixture containing methyl methacrylate (60 parts by weight), ethylene glycol dimethacrylate (30 parts by weight), and poly(ethylene glycol-propylene glycol) monomethacrylate ("Blemmer® 50 PEP-300") (10 parts by weight), to prepare a mixed solution.

Next, deionized water (500 parts by weight) as an aqueous medium in which sodium lauryl sulfate (0.05 parts by weight) as an anionic surfactant had been dissolved was put into a polymerization vessel equipped with a stirrer and a thermometer. In this deionized water, tribasic calcium phosphate (50 parts by weight) as a poorly water-soluble inorganic salt was dispersed to obtain a dispersion liquid. The mixed solution prepared in advance was put in this dispersion liquid. The obtained dispersion liquid was stirred for 10 minutes with a high-speed emulsification and dispersion device ("T.K homo-mixer" manufactured by PRIMIX Corporation) at a stirring rate of 5,000 rpm so that the mixed solution could produce droplets with diameters of about 5 µm. Next, the polymerization vessel was heated to 65° C. to carry out suspension polymerization while stirring. The polymerization vessel was subsequently cooled down. The obtained suspension was filtered, washed, and then dried, to obtain resin particles.

Figure 13:
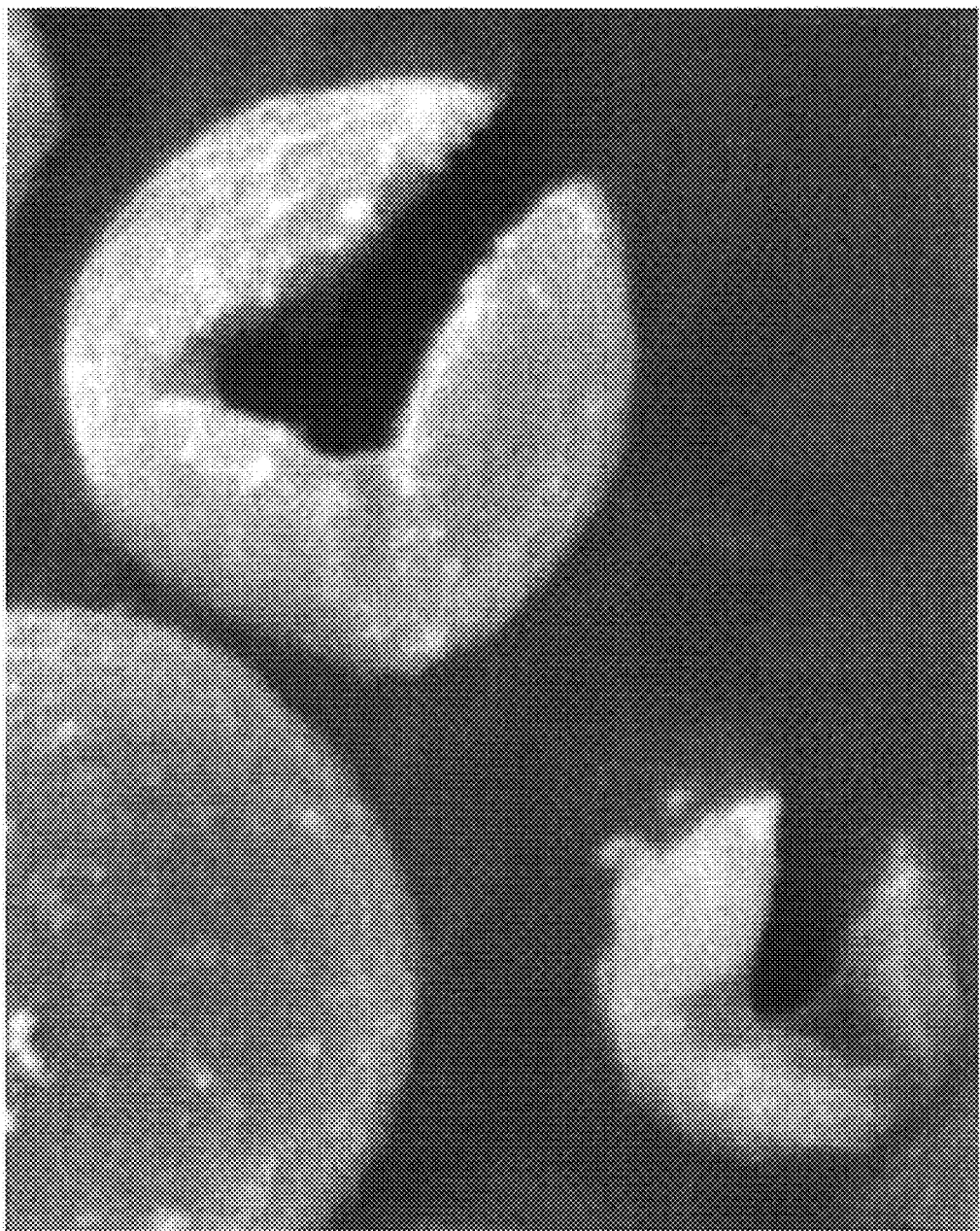
FIG. 13 is an SEM image generated by SEM-imaging the surface of non-spherical resin particles obtained in example 5 of the present invention.

The obtained resin particles were imaged under an SEM, to obtain the SEM image in FIG. 13. The obtained resin particles were non-spherical and had a horseshoe-like cross-section as illustrated in FIG. 13. The particle diameter A, notch section depth B, and notch section opening width C of the obtained non-spherical resin particles with a horseshoe-like cross-section were measured according to the aforementioned measuring method (A=5.2 µm, B=3.5 µm, C=2.1 µm). The sphere-equivalent volume-average particle diameter of the non-spherical resin particles measured according to the aforementioned measuring method was 5.1 µm.

Figure 14:
FIG. 14 is a TEM image generated by TEM-imaging the cross-section of a non-spherical resin particle obtained in example 5 of the present invention.

The obtained non-spherical resin particles with a horseshoe-like cross-section were embedded in an embedding resin (epoxy resin). Subsequently, some non-spherical resin particles embedded in the embedding resin were cut to obtain thin pieces of them including their centers. The thin pieces were stained with a stain (ruthenium tetroxide) and imaged under a TEM to obtain the TEM image in FIG. 14. The obtained non-spherical resin particles with a horseshoe-like cross-section, as illustrated in FIG. 14, had a first resin component (thick colored, larger gray portion) derived from the monomer mixture containing the crosslinking monomer and a second resin component (thin colored, smaller gray portion) derived from the 2,2,2-trifluoroethyl methacrylate-methyl methacrylate copolymer, with the second resin component residing locally near the surface of the non-spherical resin particles. Besides, the obtained non-spherical resin particles with a horseshoe-like cross-section, as illustrated in FIG. 14, had more than half of their notch section surface formed of the second resin component and the rest of their surface formed of the first resin component. Note that in the TEM image in FIG. 14, the black portions present in the first resin component surface are caused by the stain that had entered the interface between the non-spherical resin particle and the embedding resin and are no indication of presence of a component other than the first and second resin components in the non-spherical resin particle.

Example 6

The same procedures were followed as in example 3, except that the seed particle-containing emulsion (360 grams) prepared in exemplary seed particle preparation 4 was used in place of the seed particle-containing emulsion (360 grams) prepared in exemplary seed particle preparation 1, to obtain resin particles.

Figure 15:
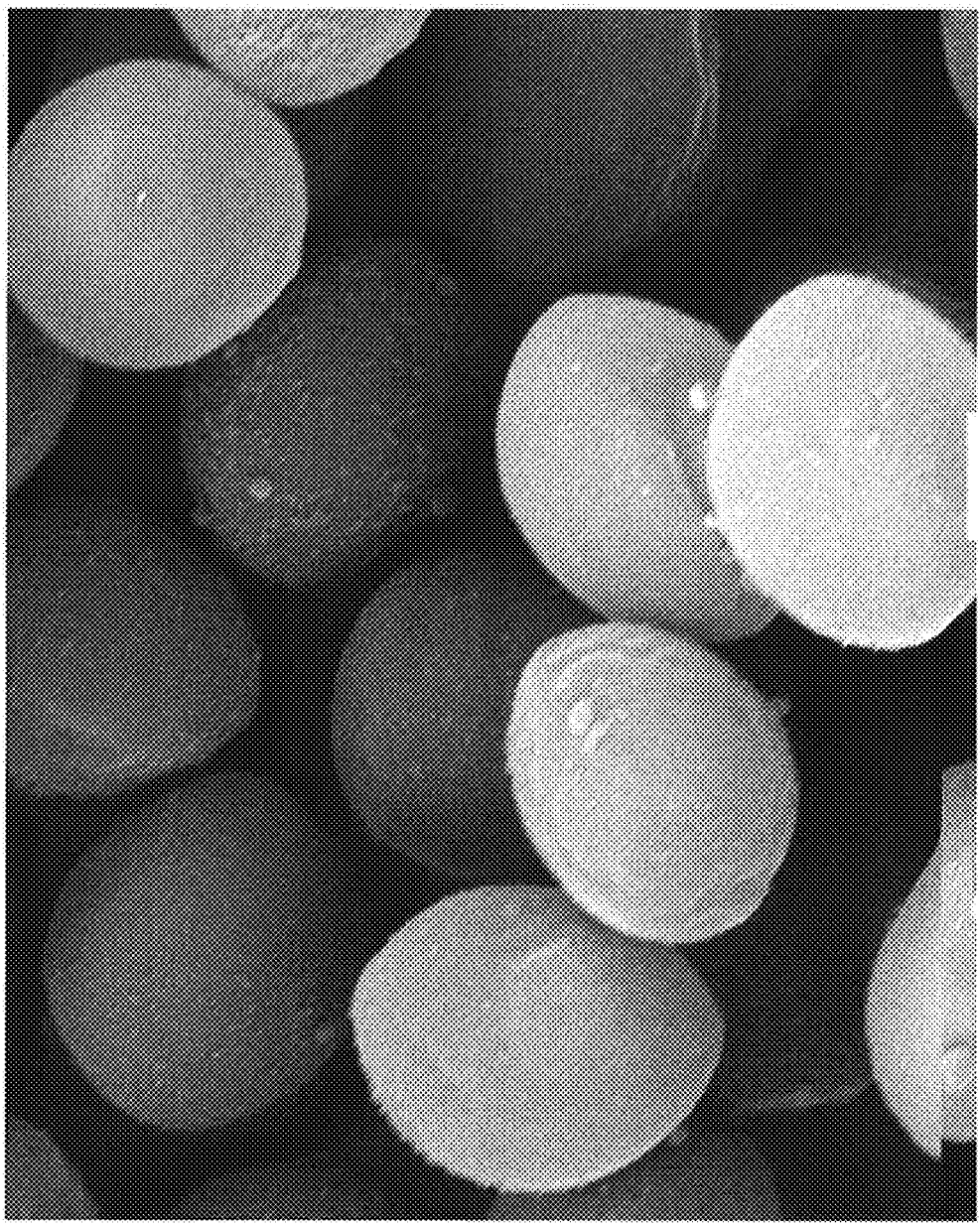
FIG. 15 is an SEM image generated by SEM-imaging the surface of non-spherical resin particles obtained in example 6 of the present invention.

The obtained resin particles were imaged under an SEM, to obtain the SEM image in FIG. 15. The obtained resin particles were non-spherical (biconvex lens-shaped) as illustrated in FIG. 15. The particle diameter A of the obtained non-spherical (biconvex lens-shaped) resin particles, the height H of the larger planoconvex lens-shaped section, and the height I of the smaller planoconvex lens-shaped section were measured according to the aforementioned measuring method (A=2.90 μm, H=1.13 μm, I=0.80 μm, H/A=0.390, I/A=0.276).

Figure 16:
FIG. 16 is a TEM image generated by TEM-imaging the cross-section of a non-spherical resin particle obtained in example 6 of the present invention.

The obtained non-spherical (biconvex lens-shaped) resin particles were embedding in an embedding resin (epoxy resin). Subsequently, some non-spherical resin particles embedded in the embedding resin were cut to obtain thin pieces of them including their centers. The thin pieces were stained with a stain (ruthenium tetroxide) and imaged under a TEM to obtain the TEM image in FIG. 16. The obtained non-spherical (biconvex lens-shaped) resin particles, as illustrated in FIG. 16, had a first resin component (thin colored, larger gray portion) derived from the monomer mixture containing the crosslinking monomer and a second resin component (thick colored, smaller gray portion) derived from seed particles, with the second resin component residing locally near the surface of the non-spherical resin particles. Besides, the obtained non-spherical (biconvex lens-shaped) resin particles, as illustrated in FIG. 16, had the substantially entire surface of their smaller planoconvex lens-shaped section formed of the second resin component and the rest of their surface formed of the first resin component.

Example 7

The same procedures were followed as in example 1, except that methoxypolyethylene glycol monomethacrylate ("Blemmer® PME-400" manufactured by NOF Corporation, a mixture of compounds of general formula (1) where $R_1$ was $CH_3$, $R_2$ was $C_2H_5$, $R_4$ was $CH_3$, m was 9 on average, and n was 0) was used in place of poly(ethylene glycol-propylene glycol)monomethacrylate (100 grams) and also that the seed particle-containing emulsion (360 grams) prepared in exemplary seed particle preparation 4 was used in place of the seed particle-containing emulsion (360 grams) prepared in exemplary seed particle preparation 1, to obtain resin particles.

Figure 17:
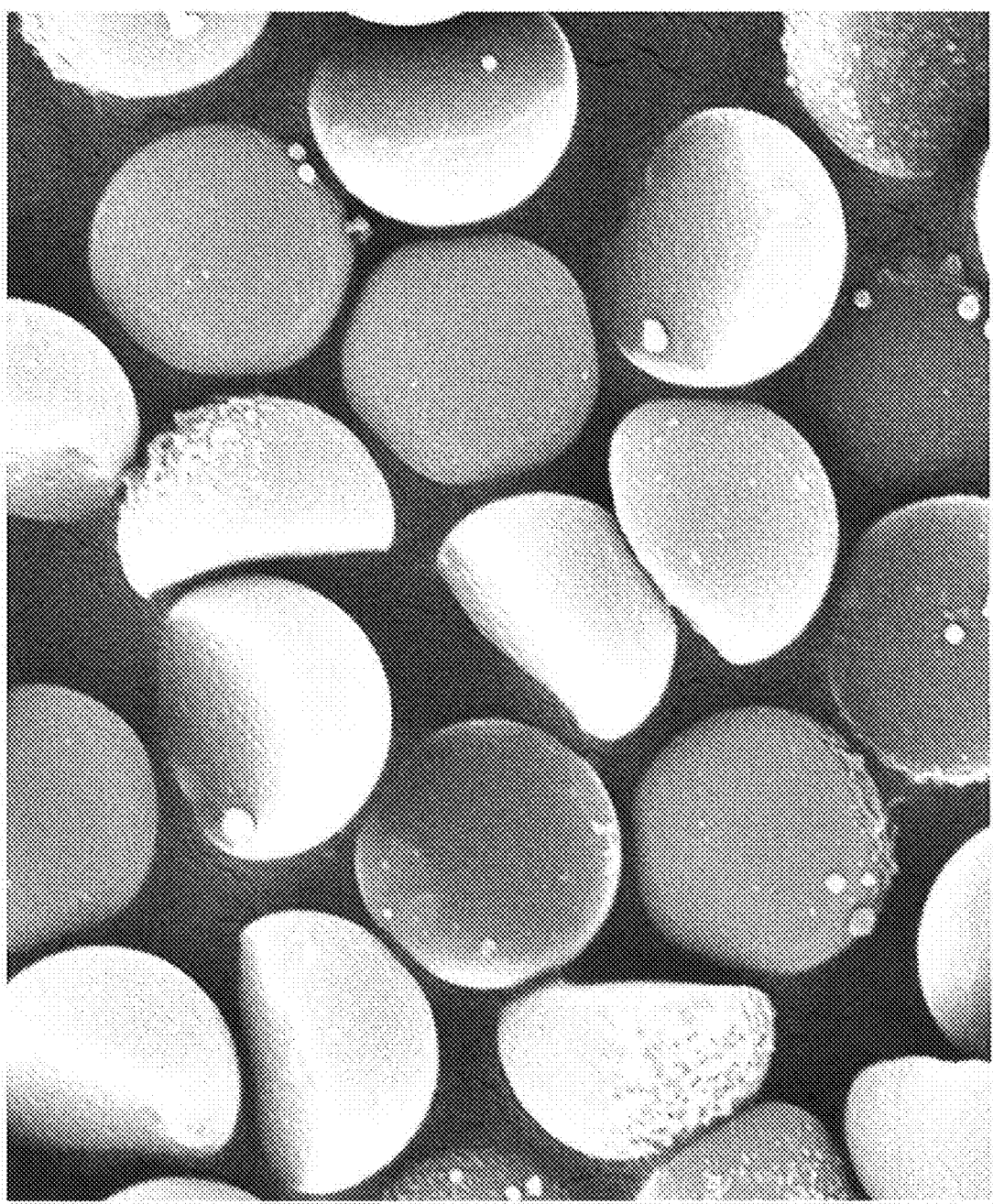
FIG. 17 is an SEM image generated by SEM-imaging the surface of non-spherical resin particles obtained in example 7 of the present invention.

The obtained resin particles were imaged under an SEM, to obtain the SEM image in FIG. 17. The obtained resin particles were non-spherical (semi-spherical) as illustrated in FIG. 17. The particle diameter A and minor axis F of the obtained non-spherical (semi-spherical) resin particles were measured according to the aforementioned measuring method (A=2.90 μm, F=1.60 μm, and F/A=0.552). The sphere-equivalent volume-average particle diameter of the non-spherical resin particles measured according to the aforementioned measuring method was 2.65 μm.

Figure 18:
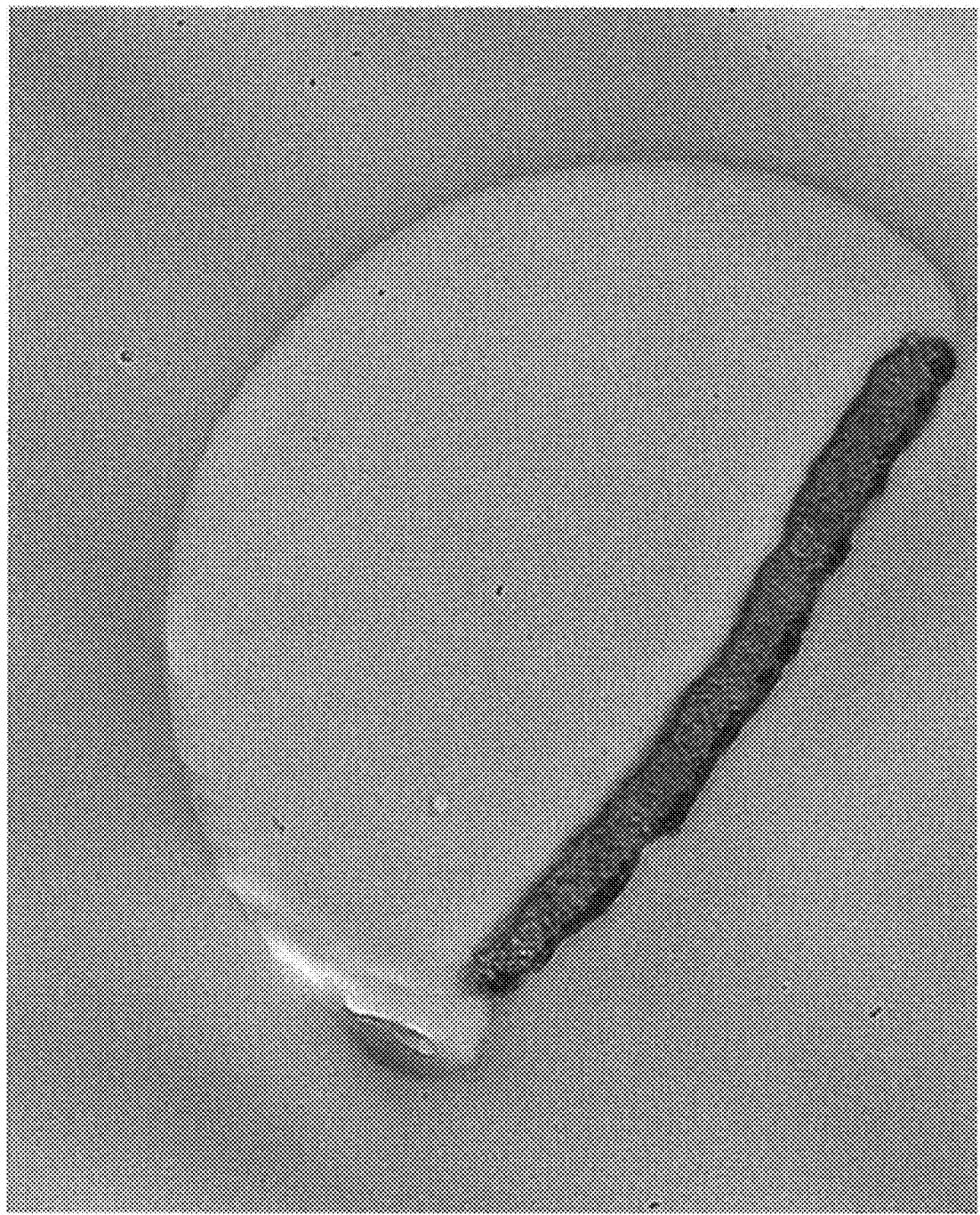
FIG. 18 is a TEM image generated by TEM-imaging the cross-section of a non-spherical resin particle obtained in example 7 of the present invention.

The obtained non-spherical (semi-spherical) resin particles were embedded in an embedding resin (epoxy resin). Subsequently, some non-spherical resin particles embedded in the embedding resin were cut to obtain thin pieces of them including their centers. The thin pieces were stained with a stain (ruthenium tetroxide) and imaged under a transmission electron microscope (TEM) to obtain the TEM image in FIG. 18. The obtained non-spherical (semi-spherical) resin particles, as illustrated in FIG. 18, had a first resin component (thin colored, larger gray portion) derived from the monomer mixture containing the crosslinking monomer and a second resin component (thick colored, smaller gray portion) derived from seed particles, with the second resin component residing locally near the surface of the non-spherical resin particles. Besides, the obtained non-spherical (semi-spherical) resin particles, as illustrated in FIG. 18, had the substantially entire surface of their plane portion formed of the second resin component and the rest of their surface formed of the first resin component.

Comparative Example 1

The same procedures were followed as in example 1, except that the seed particle-containing emulsion (360 grams) prepared in exemplary seed particle preparation 3 was used in place of the seed particle-containing emulsion (360 grams) prepared in exemplary seed particle preparation 1, to obtain resin particles.

The obtained resin particles were observed under an SEM and turned out to be spherical. The average particle diameter of the obtained resin particles was 2.54 μm.

Example 8

Exemplary External Preparation Manufacture

The non-spherical (semi-spherical) resin particles obtained in example 1 (20.0 parts by weight), sericite (6.0 parts by weight) as a clay mineral, titanium dioxide (3.0 parts by weight), and a suitable amount of pigment were mixed to prepare a powder portion.

Apart from the powder portion, triethanol amine (1.0 parts by weight) as a pH adjuster and VEEGUM® (manufactured by R.T. Vanderbilt Company, Inc.) (0.5 parts by weight) as a clay mineral were added to purified water (50 parts by weight) and heated to dissolve. The previously prepared powder portion was added to the solution thus obtained, dispersed uniformly in the solution by a homomixer, and subsequently maintained at 70° C., to obtain an aqueous phase component.

Next, apart from the aqueous phase component, stearic acid (2.0 parts by weight), cetyl alcohol (0.3 parts by weight), liquid paraffin (20.0 parts by weight), a suitable amount of perfume, and a suitable amount of antiseptic were mixed. The mixture was heated to dissolve, and subsequently maintained at 70° C., to obtain an oil phase component.

Figure 19:
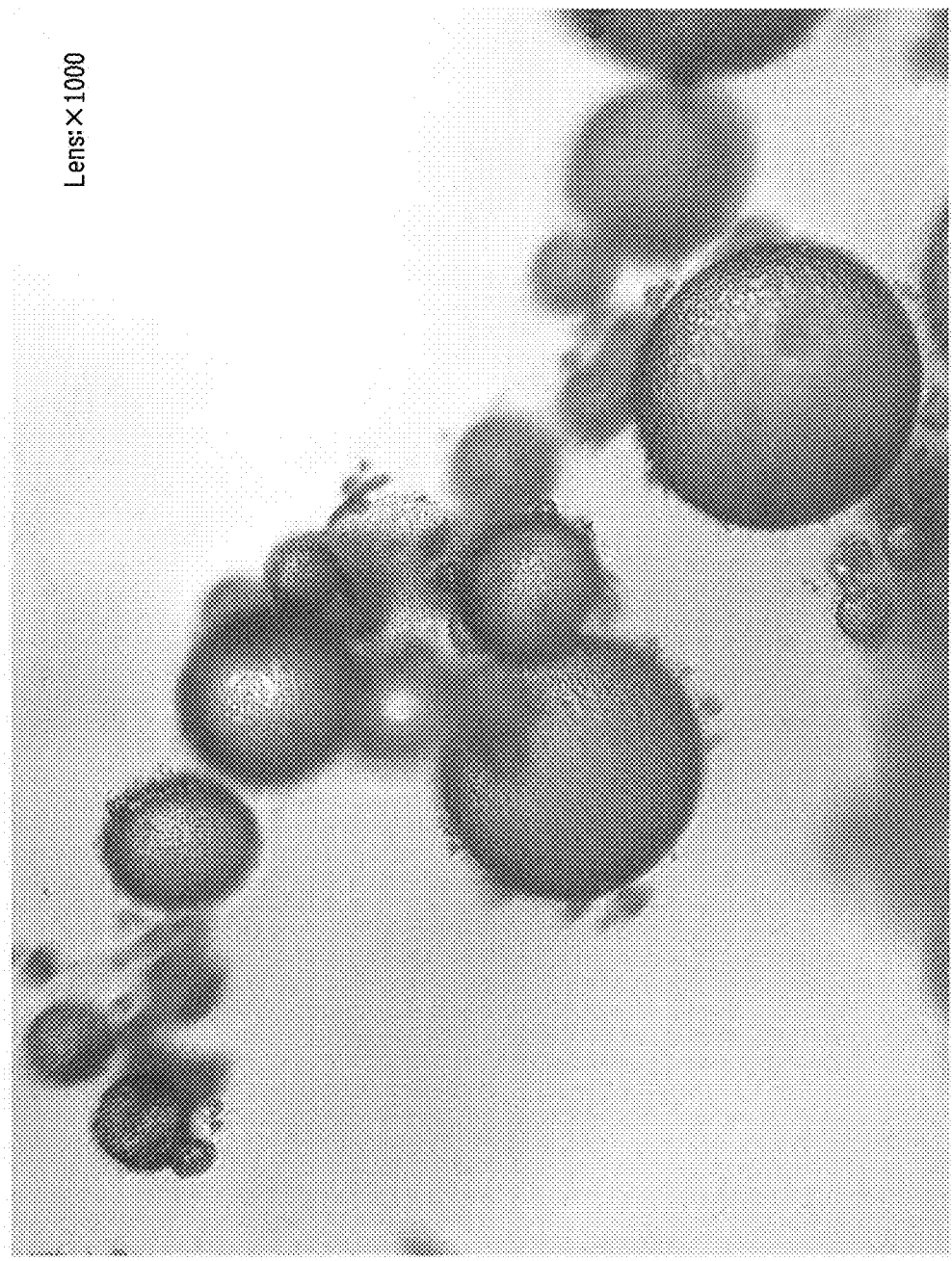
FIG. 19 is an image generated by imaging emulsion-type makeup foundation obtained in example 8 of the present invention under an optical microscope.

The aqueous phase component was added to the obtained oil phase component. The mixture was preliminarily emulsified, then emulsified and dispersed uniformly by a homomixer, and subsequently cooled down while stirring, to obtain an emulsion-type makeup foundation (emulsion cosmetic) in which the oil phase component is dispersed in the aqueous phase component. The obtained emulsion-type makeup foundation was imaged under an optical microscope (×1,000 times) to obtain an image that is shown in FIG. 19. The image shows that non-spherical resin particles were present on the surface of droplets.

Comparative Example 2

Comparative Example of External Preparation Manufacture

The same procedures were followed as in example 8, except that the spherical resin particles obtained in comparative example 1 were used in place of the non-spherical (semi-spherical) resin particles obtained in example 1, to obtain a comparative emulsion-type makeup foundation (emulsion cosmetic).

The emulsion-type makeup foundation obtained in comparative example 2 lacked emulsification stability. Separation of the oil phase component and the aqueous phase component was observed. Meanwhile, the emulsion-type makeup foundation obtained in example 8 had stable emulsification. In addition, the emulsion-type makeup foundation obtained in example 8 exhibited excellent slippage and gave a smooth and very comfortable feel in skin application when compared with the emulsion-type makeup foundation obtained in comparative example 2. Besides, the emulsion-type makeup foundation obtained in example 8 was able to fix skin flaws (cover up spots, freckles, pores, etc.) when it was applied to skin.

Example 9

Exemplary Optical Member Manufacture

The non-spherical (semi-spherical) resin particles obtained in example 1 (5 parts by weight) were mixed with isopropanol (10 parts by weight) and stirred for 3 minutes by a centrifugal stirrer, to obtain a dispersion liquid. The dispersion liquid was gently spread, using a dropper, over a water surface in a beaker containing distilled water. Thereafter, a PET film as a transparent film base material was placed on the water surface to transfer the spread dispersion liquid onto the PET film. The PET film, carrying the dispersion liquid thereon, was dried for 1 hour in an oven that was kept at 70° C., to obtain a light diffusing film as a form of light diffuser (a form of optical member).

Figure 20:
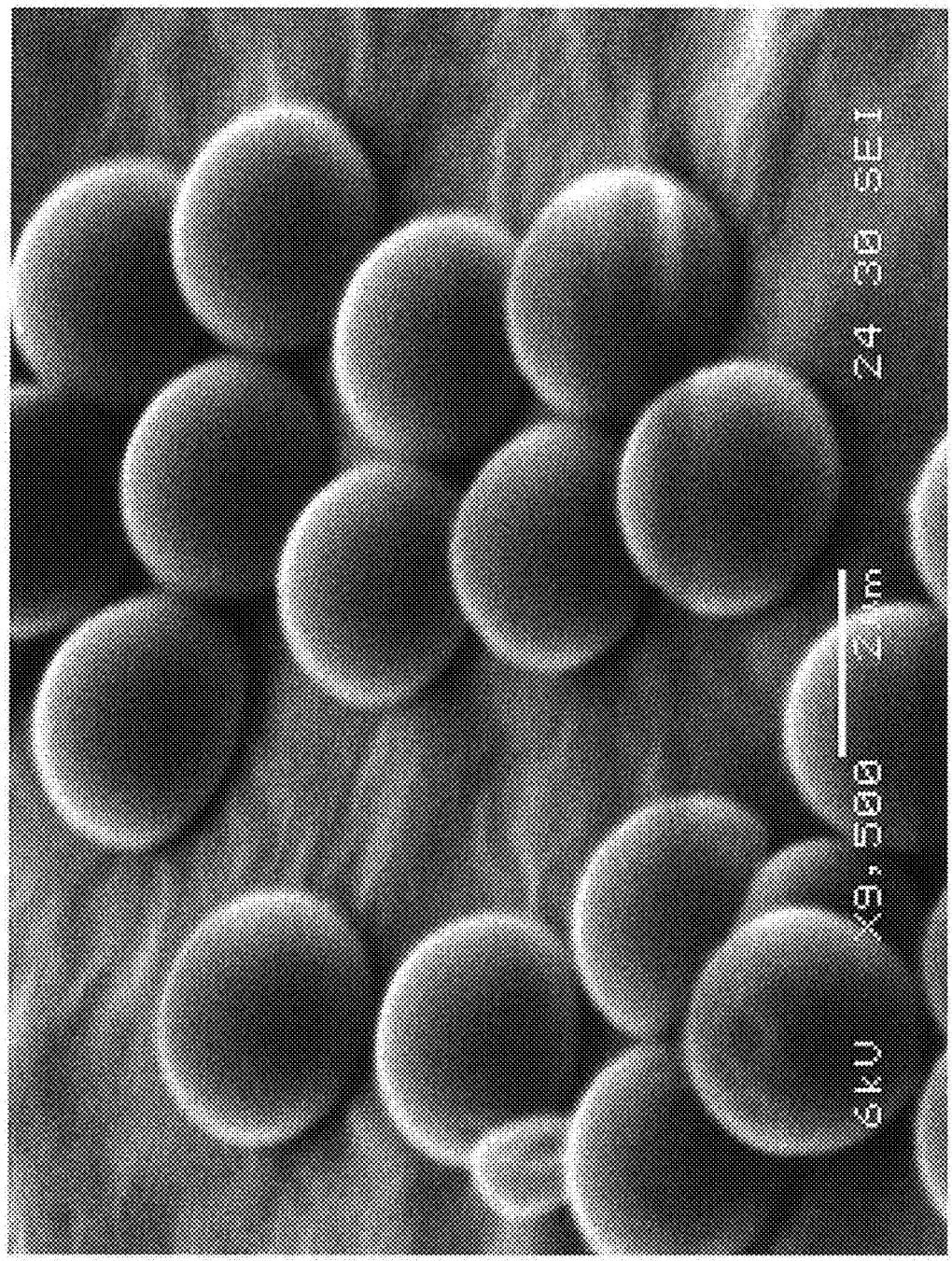
FIG. 20 is an SEM image generated by SEM-imaging a light diffusing film obtained in example 9 of the present invention.

The obtained light diffusing film were observed under an SEM, and it was found, as illustrated in FIG. 20, that the non-spherical (semi-spherical) resin particles were arranged on the PET film with their plane portions facing the PET film.

The arrangement was achieved presumably due to the following mechanism. The non-spherical (semi-spherical) resin particles obtained in example 1 had the substantially entire surface of their plane portion formed of the second, hydrophobic resin component derived from the seed particles and the rest of their surface formed of the first, hydrophilic resin component derived from the monomer mixture containing the crosslinking monomer. When the isopropanol dispersion liquid was spread on the surface of distilled water, the first, hydrophilic resin component, disposed at the interface between the distilled water and the isopropanol, faced the water surface, whereas the second, hydrophobic resin component faced the isopropanol.

The light diffusing film obtained in the present example includes non-spherical resin particles arranged on a PET film in such a manner that the plane portions of the non-spherical resin particles face the PET film. Hence, the light diffusing film controls the direction of the light diffused at the surface of the non-spherical resin particles so that the diffused rays travel in directions closer to the normal to the PET film surface (front direction), or in other words, converges the diffused rays so that they travel in directions closer to the front direction. Therefore, when the light diffusing film is incorporated into optical apparatus (e.g., a liquid crystal display device), the light diffusing film will, apart from achieving the excellent light diffusion effect, improve the luminance of the optical apparatus in the front direction (luminance observed when viewed normal to the front face of the optical apparatus).

REFERENCE SIGNS LIST 1, 4, 11 First Resin Component
2, 5, 12 Second Resin Component
3 Notch Section
6 Cap Section
7 Stem Section
13 Plane Portion
16, 17 Planoconvex Lens-shaped Section

The invention claimed is:

1. Non-spherical resin particles, each having a circular outline when viewed from a direction in which a maximum projected area is produced and a non-circular outline when viewed from a direction in which a minimum projected area is produced,
    each of the non-spherical resin particles comprising a first resin component and a second resin component which is different from the first resin component, the second resin component residing locally near a surface of that particle, wherein:
    the first resin component is a hydrophilic resin, and the second resin component is a hydrophobic resin, and
    the hydrophobic resin is a homopolymer or a copolymer of a (meth)acrylic acid ester having a $C_2$-$C_{10}$ halogenated alkyl group in an ester moiety thereof.

2. The non-spherical resin particles as set forth in claim 1, wherein:
    each of the non-spherical resin particles has a partly missing sphere shape;
    the missing part has a surface at least a part of which is formed of the second resin component; and
    the rest of the surface of the particle is formed of the first resin component.

3. The non-spherical resin particles as set forth in claim 1, wherein said particles are semi-spherical.

4. The non-spherical resin particles as set forth in claim 1, wherein said particles are shaped like a biconvex lens.

5. The non-spherical resin particles as set forth in claim 1, wherein said particles are shaped like a mushroom.

6. The non-spherical resin particles as set forth in claim 1, wherein said particles have a horseshoe-like cross-section.

7. A method of manufacturing non-spherical resin particles, comprising either
    the set of steps of:
        allowing particles of a resin to absorb a vinyl-based polymerizable monomer contained in an aqueous emulsion; and
        polymerizing the absorbed vinyl-based polymerizable monomer or
    the set of steps of:
        dissolving a resin in a vinyl-based polymerizable monomer to prepare a solution; and
        polymerizing the solution in an aqueous medium,
    wherein:
    the resin has a moiety derived from a (meth)acrylic acid ester having in an ester moiety thereof a $C_2$-$C_{10}$ halogenated alkyl group and has a weight-average molecular weight of from 150,000 to 1,000,000 as measured by gel permeation chromatography; and the vinyl-based polymerizable monomer contains a crosslinking monomer in an amount of 5 to 50 wt % as based on a total amount of the vinyl-based polymerizable monomer.

8. The method as set forth in claim 7, wherein the vinyl-based polymerizable monomer contains a (meth)acrylic acid ester having an alkylene oxide group of a general formula:

where $R_1$ is either H or $CH_3$, $R_2$ and $R_3$ are different $C_2$-$C_5$ alkylene groups, m and n are numbers from 0 to 50, at least either m or n being not 0, and $R_4$ is either H or $CH_3$.

9. An emulsifier comprising non-spherical resin particles as set forth in claim 1.

10. An external preparation comprising non-spherical resin particles as set forth in claim 1.

11. An emulsion comprising non-spherical resin particles as set forth in claim 1.

12. A coating agent comprising non-spherical resin particles as set forth in claim 1.

13. A light diffuser comprising non-spherical resin particles as set forth in claim 1.

14. An optical member comprising a base material and the non-spherical resin particles as set forth in claim 1, wherein the non-spherical resin particles are semi-spherical and arranged on the base material so that plane portions thereof face the base material.

15. The optical member as set forth in claim 14, serving as a light diffusing film, wherein the base material is a transparent film base material.

* * * * *